(12) United States Patent
Youn et al.

(10) Patent No.: US 8,685,409 B2
(45) Date of Patent: Apr. 1, 2014

(54) INFLUENZA T-CELL IMMUNIZATION AGAINST DIVERSE INFLUENZA A VIRUSES

(71) Applicant: Mogam Biotechnology Research Institute, Yongin-si (KR)

(72) Inventors: Jin-Won Youn, Yongin-si (KR); Ji-Sun Kwon, Yongin-si (KR); Jung-Soon Yoon, Yongin-si (KR); Yeon-Jung Kim, Yongin-si (KR)

(73) Assignee: Mogam Biotechnology Research Institute, Yongin-Si (KR)

( * ) Notice: Subject to any disclaimer, the term of this patent is extended or adjusted under 35 U.S.C. 154(b) by 0 days.

(21) Appl. No.: 13/666,467

(22) Filed: Nov. 1, 2012

(65) Prior Publication Data

US 2013/0259886 A1 Oct. 3, 2013

(30) Foreign Application Priority Data

Mar. 30, 2012 (KR) .......................... 10-2012-0033317

(51) Int. Cl.
*A61K 39/145* (2006.01)

(52) U.S. Cl.
USPC .................... 424/206.1; 424/204.1; 536/23.72

(58) Field of Classification Search
None
See application file for complete search history.

(56) References Cited

PUBLICATIONS

GI:4584893 GenBank Accession # AF073185, Influenza A virus (A/Chicken/New York/13833-7/95 (H7N2NSB)) matrix protein 1 (M1) and matrix protein 2 (M2) genes, complete cds., Apr. 23, 1999.*
GI:134044357 GenBank Accession #CY011035, Influenza A virus (A/blue-winged teal/Ohio/926/2002(H3N8)) segment 1, complete sequence, Apr. 13, 2007.*
GI:323984 GenBank Accession #M22574, Influenza A virus (A/duck/Bavaria/2/1977(H1N1)) nucleoprotein gene, complete cds, Jul. 13, 2006.*
GI:82654856 GenBank Accession #CY005794, Influenza A virus (A/turkey/Italy/4169/1999(H7N1)) segment 2, complete sequence, Sep. 25, 2006.*
GI:78097605 GenBank Accession #CY005610, Influenza A virus (A/chicken/Hong Kong/17/1977(H6N1)) segment 3, complete sequence, Sep. 25, 2006.*

* cited by examiner

*Primary Examiner* — Louise Humphrey
(74) *Attorney, Agent, or Firm* — Sughrue Mion, PLLC

(57) ABSTRACT

There is provided a T cell-based universal influenza vaccine including internal genes capable of preparing against infection by broad hetero-subtypic influenza viruses, and thereby preparing for unpredictable epidemic influenza. The present invention selected internal genes of the consensus sequence obtained from bird, pig, and human influenza isolates in order to develop the T cell-based universal flu vaccine. The T cell-based universal flu vaccine according to the present invention is characterized by including at least one CTL epitope, by containing a plurality of internal genes and using the entire sequence of the internal gene itself. The T cell-based universal flu vaccine can achieve broad defense in infection with hetero-subtypic influenza viruses.

10 Claims, 26 Drawing Sheets

FIG. 2

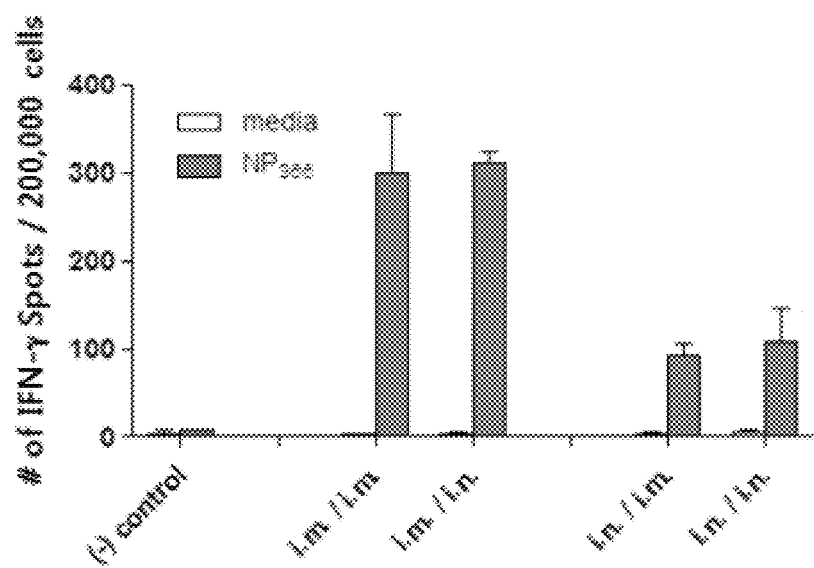

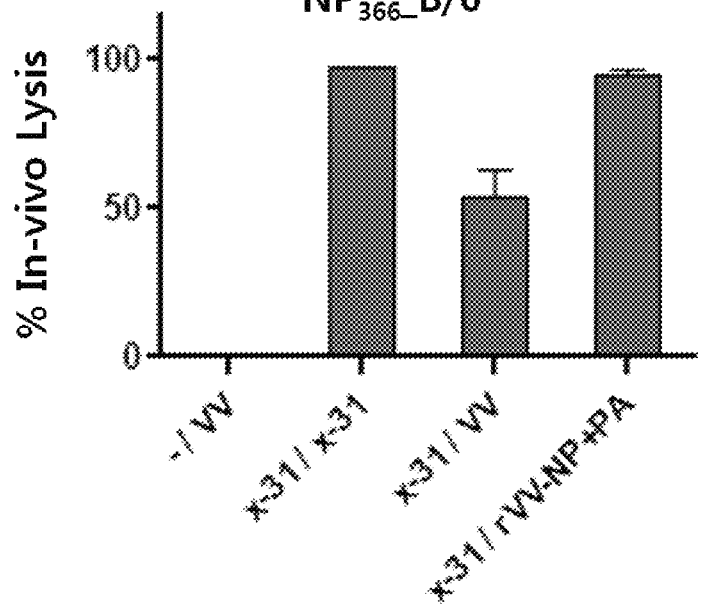

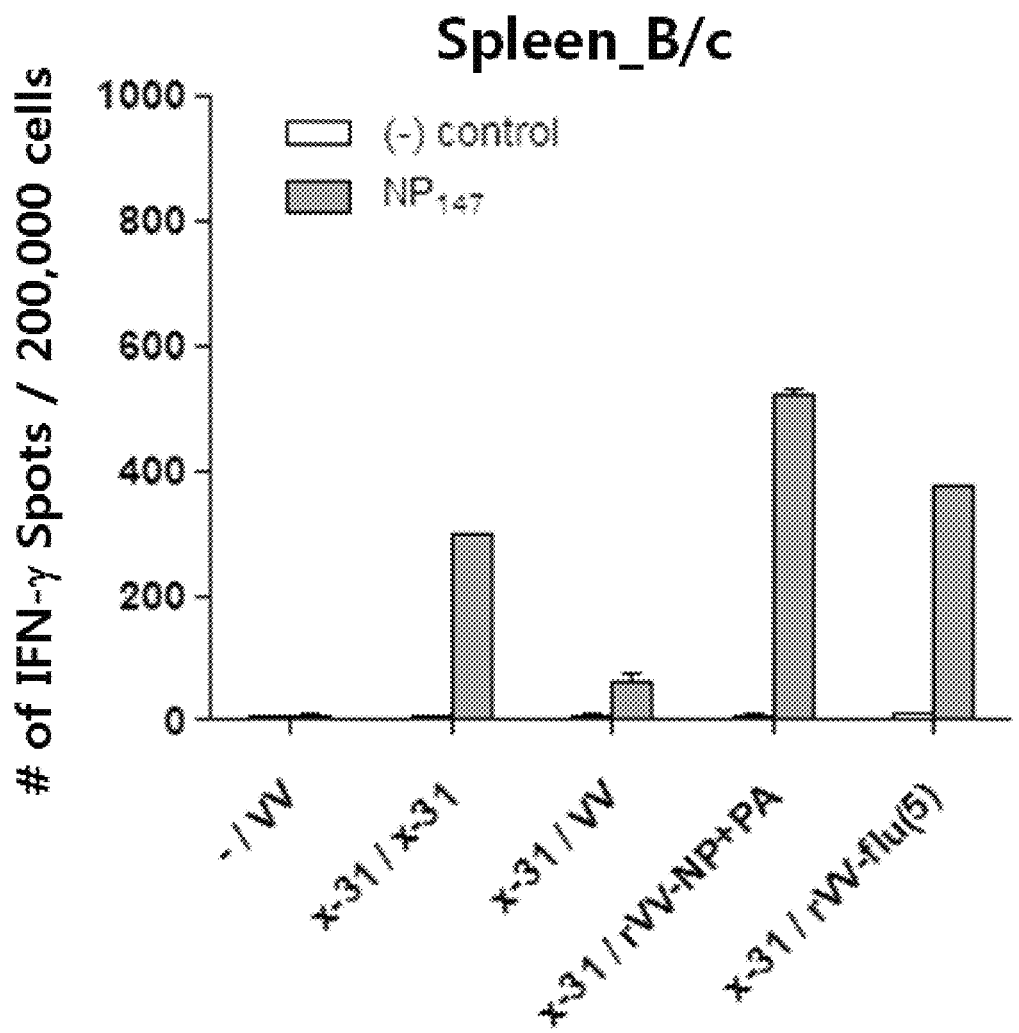

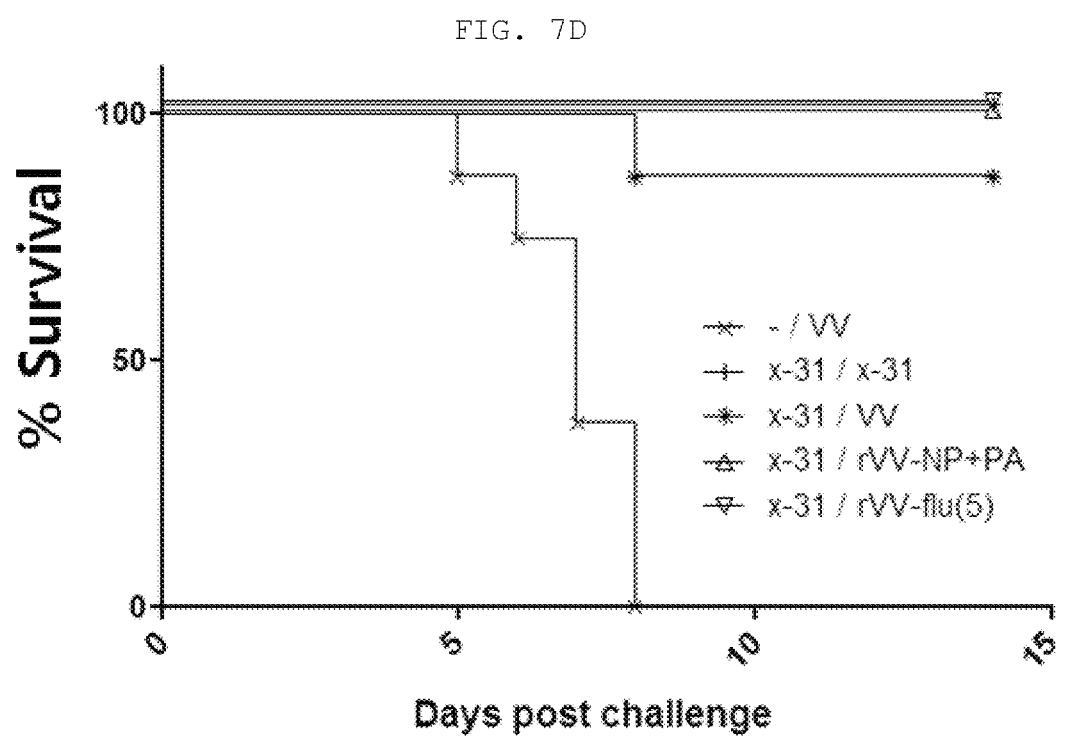

%Weight Loss vs Days post challenge

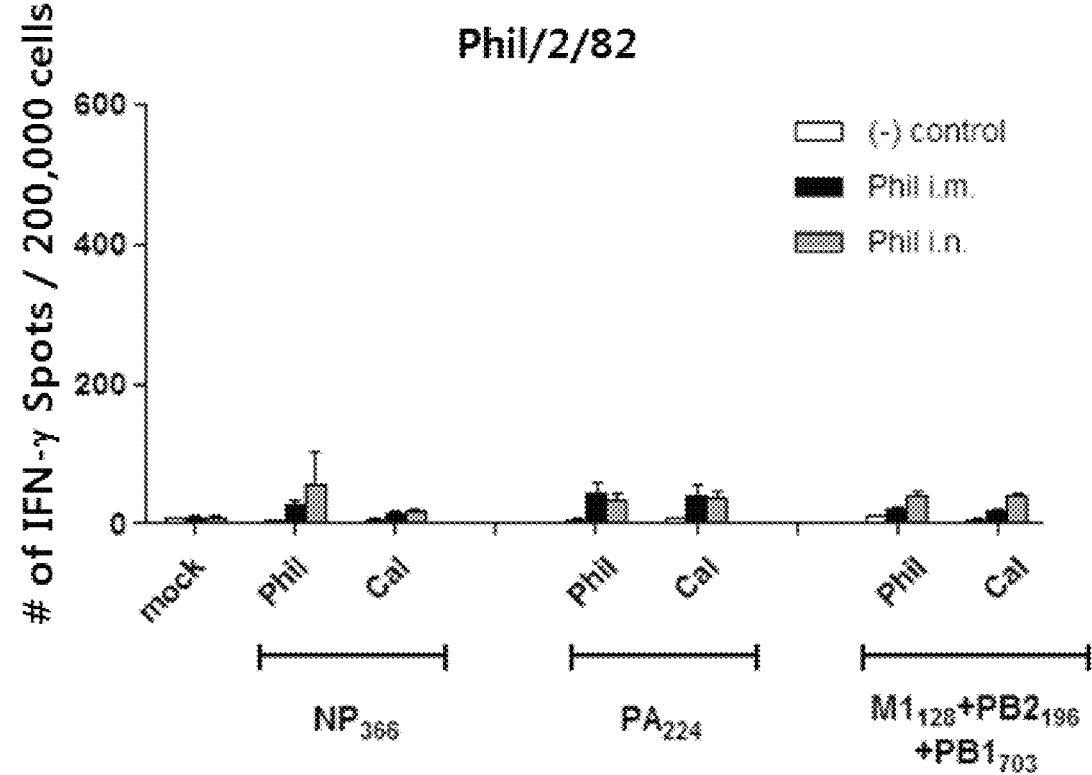

FIG. 10A

100 LD$_{50}$ Cal/04/09_B/6

% Weight Loss vs Days post challenge

FIG. 10B

SEQUENCE LISTING

```
<160> NUMBER OF SEQ ID NOS: 84

<210> SEQ ID NO 1
<211> LENGTH: 1565
<212> TYPE: DNA
<213> ORGANISM: Influenza A virus

<400> SEQUENCE: 1
agcaaaagca gggtagataa tcactcactg agtgacatcc acaacatggc gtctcaaggc      60
accaaacgat cttatgagca gatggaaact ggtggagagc gccagaatgc tactgagatc     120
agagcatctg ttgggagaat ggtaggtgga attggaagat tctacataca gatgtgcact     180
gaactcaaac tcagcgacta tgaagggagg ctgatccaga acagcataac aatagagaga     240
atggttctct ctgcgtttga tgaaaggagg aacaaatacc tggaagagca ccccagtgcg     300
ggaaaggacc ctaagaaaac tggaggtccg atttacagaa ggagggatgg aaaatggatg     360
agggagctga ttctgtatga caaagaggaa ataaggagga tctggcgcca ggcgaacaat     420
ggagaagacg caactgctgg tctcacccac ctgatgatct ggcattccaa cctgaatgat     480
gccacatatc agagaacaag agctctcgtg cgtactggga tggaccccag aatgtgctct     540
ctgatgcaag gatcaactct cccgaggaga tctggggcag ctggtgcagc agtgaaggga     600
gttggaacga tggtgatgga gctgattcgg atgataaagc ggggaatcaa tgatcggaac     660
```

-continued

```
ttctggagag gcgaaaatgg acggagaaca aggattgcat atgagagaat gtgcaacatc    720
ctcaaaggaa aattccaaac agcagcacaa cgagcaatga tggatcaggt gcgagaaagc    780
aggaatcctg ggaatgctga aattgaagac cttatctttc tggcacggtc tgcactcatt    840
ctgagaggat cagtggccca taagtcctgc ctgcctgctt gtgtatatgg acttgcagtg    900
gccagtgggt acgactttga gagagagggc tactctctgg ttggaataga tccttttcgc    960
ttgcttcaaa acagccaggt gttcagcctc attagaccaa atgaaaatcc agcacataaa   1020
agccaactag tatggatggc atgccactct gcagcatttg aagacctgag agtgtcaagc   1080
tttatcagag ggacaagagt ggtcccaaga ggacaactgt ccaccagagg agttcaaatt   1140
gcttcaaatg agaacatgga aacaatggac tccagtactc ttgaactgag gagcagatac   1200
tgggctataa ggaccaggag cggaggaaac accaaccaac agagagcatc ggcagggcaa   1260
atcagcgtac aacctacttt ctcggtacag aggaatcttc ctttcgagag agcgaccatc   1320
atggcggcat ttacagggaa cactgaaggc agaacatctg acatgaggac tgagatcata   1380
agaatgatgg aaagtgccag accagaagat gtgtctttcc aggggcgggg agtcttcgag   1440
ctctcggacg aaaaggcaac gaacccgatc gtgccttcct ttgacatgag taatgaggga   1500
tcttatttct tcggagacaa tgcagaggag tatgacaatt aaagaaaaat accttgtttc   1560
tact                                                                1565
```

<210> SEQ ID NO 2
<211> LENGTH: 498
<212> TYPE: PRT
<213> ORGANISM: Influenza A virus

<400> SEQUENCE: 2

```
Met Ala Ser Gln Gly Thr Lys Arg Ser Tyr Glu Gln Met Glu Thr Gly
 1               5                  10                  15

Gly Glu Arg Gln Asn Ala Thr Glu Ile Arg Ala Ser Val Gly Arg Met
            20                  25                  30

Val Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Ile Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Arg Asp Gly Lys Trp Met Arg Glu Leu Ile Leu Tyr Asp
            100                 105                 110

Lys Glu Glu Ile Arg Arg Ile Trp Arg Gln Ala Asn Asn Gly Glu Asp
        115                 120                 125

Ala Thr Ala Gly Leu Thr His Leu Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
        195                 200                 205
```

Gly Glu Asn Gly Arg Arg Thr Arg Ile Ala Tyr Glu Arg Met Cys Asn
            210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Leu Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Phe Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Ser Ser Phe Ile Arg Gly Thr Arg Val
            340                 345                 350

Val Pro Arg Gly Gln Leu Ser Thr Arg Gly Val Gln Ile Ala Ser Asn
        355                 360                 365

Glu Asn Met Glu Thr Met Asp Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Thr Phe Ser Val Gln Arg
                405                 410                 415

Asn Leu Pro Phe Glu Arg Ala Thr Ile Met Ala Ala Phe Thr Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn

<210> SEQ ID NO 3
<211> LENGTH: 2233
<212> TYPE: DNA
<213> ORGANISM: Influenza A virus

<400> SEQUENCE: 3
agcgaaagca ggtactgatt caaaatggaa gattttgtgc gacaatgctt caatccaatg    60
atcgtcgagc ttgcggaaaa ggcaatgaaa gaatatgggg aggatccgaa atcgaaacg    120 aacaaattcg ctgcaatatg cacacacctg gaagtctgtt tcatgtattc ggatttccac    180
ttcattgacg aaaggggcga atcaattatt gtagaatccg gtgacccaaa tgcattactg    240
aaacaccgat tcgagataat tgaaggaaga gaccggacaa tggcctggac agtggttaat    300
agtatctgca acaccacagg agtcgagaag cctaaatttc ttccagatct gtatgattac    360
aaagaaaacc gattcattga atcggagtg acacggagag aagtccacat ctattaccta    420
gaaaaagcca acaagataaa gtcagaaaag acacacattc acatttctc attcactgga    480

-continued

```
gaggaaatgg ccaccaaagc agattacacc cttgatgaag aaagtagagc aagaatcaaa     540
accaggctgt tcaccatcag acaagaaatg gccagcaggg gtttgtggga ttcctttcgt     600
cagtccgaga gaggcgaaga gacaattgaa gaaagatttg aaatcacagg gaccatgcgc     660
aggcttgccg accaaagtct cccaccgaac ttctccagcc ttgaaaactt tagagcctat     720
gtggatggat tcgaaccgaa cggctgcatt gagggcaagc tttctcaaat gtcaaaagaa     780
gtgaatgcca gaatcgagcc atttttgaaa acaacaccac gccctctcag attacctgat     840
gggcctccct gctctcagcg gtcgaaattc ttgctgatgg atgctctaaa attgagcatt     900
gaggatccaa gtcatgaggg agaggggata ccgctatatg atgcaatcaa atgcatgaag     960
acatttttcg gctggaaaga gcccaacatt gtcaaaccac atgagaaagg cataaatccc    1020
aattacctcc tggcttggaa gcaggtgctg gcagaacttc aggacattga aaatgaggag    1080
aagattccaa aaacaaagaa catgaagaaa acaagccaat tgaagtgggc tcttggtgag    1140
aatatggcac cggagaaagt agactttgag gactgcaaag atgtgagcga cctaaaacag    1200
tatgacagtg atgagccaga gtctagatcg ctggcaagct ggattcagag cgaattcaac    1260
aaggcatgtg aattgactga ttcaagctgg atagaactcg atgagatagg agaagatgtt    1320
gccccaattg agcacattgc aagtatgagg aggaactatt ttacagcaga agtgtcccac    1380
tgcagggcca ctgagtacat aatgaaggga gtatacataa acacagcttt gctcaatgca    1440
tcttgtgcag ccatggatga cttccagctg atcccaatga taagcaaatg cagaaccaaa    1500
gaagggagac gaaaaacgaa cctgtatggg ttcatcataa aaggaaggtc tcatttgagg    1560
aatgacactg atgttgtgaa ctttgtgagt atggaatttt ctcttactga cccgaggctg    1620
gagccacaca aatgggaaaa gtattgtgtt cttgaaatag gagacatgct cctacgaaca    1680
gcaataggcc aagtgtcaag gcccatgttt ctatacgtga gaaccaatgg aacttccaaa    1740
atcaagatga agtgggggat ggaaatgagg cgctgccttc ttcagtctct tcaacagatt    1800
gagagcatga ttgaggccga gtcttctgtc aaagaaaaag acatgaccaa agagttcttt    1860
gaaaacaaat cggaaacatg gccaattgga gagtcaccca agggagtgga agaaggctcc    1920
atcggaaaag tatgcagaac cttgttagca aaatctgtat tcaacagtct atatgcatct    1980
ccacagctcg aggggttttc agctgaatcg agaaaattgc ttctcattgt tcaggcactt    2040
agggacaacc tggaacctgg aaccttcgat cttggagggc tatatgaagc aatcgaggag    2100
tgcctgatta atgatccctg ggttttgctt aacgcatctt ggttcaactc cttcctcaca    2160
catgcactga aatagttgtg gcaatgctac tatttgctat ccatactgtc caaaaaagta    2220
ccttgtttct act                                                        2233

<210> SEQ ID NO 4
<211> LENGTH: 716
<212> TYPE: PRT
<213> ORGANISM: Influenza A virus
<400> SEQUENCE: 4

Met Glu Asp Phe Val Arg Gln Cys Phe Asn Pro Met Ile Val Glu Leu
1               5                   10                  15

Ala Glu Lys Ala Met Lys Glu Tyr Gly Glu Asp Pro Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asp Glu Arg Gly Glu Ser Ile Ile Val Glu
    50                  55                  60

```

```
Ser Gly Asp Pro Asn Ala Leu Leu Lys His Arg Phe Glu Ile Ile Glu
 65                  70                  75                  80

Gly Arg Asp Arg Thr Met Ala Trp Thr Val Asn Ser Ile Cys Asn
                 85                  90                  95

Thr Thr Gly Val Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
        195                 200                 205

Gly Thr Met Arg Arg Leu Ala Asp Gln Ser Leu Pro Pro Asn Phe Ser
210                 215                 220

Ser Leu Glu Asn Phe Arg Ala Tyr Val Asp Gly Phe Glu Pro Asn Gly
225                 230                 235                 240

Cys Ile Glu Gly Lys Leu Ser Gln Met Ser Lys Glu Val Asn Ala Arg
                245                 250                 255

Ile Glu Pro Phe Leu Lys Thr Thr Pro Arg Pro Leu Arg Leu Pro Asp
            260                 265                 270

Gly Pro Pro Cys Ser Gln Arg Ser Lys Phe Leu Leu Met Asp Ala Leu
        275                 280                 285

Lys Leu Ser Ile Glu Asp Pro Ser His Glu Gly Glu Gly Ile Pro Leu
290                 295                 300

Tyr Asp Ala Ile Lys Cys Met Lys Thr Phe Phe Gly Trp Lys Glu Pro
305                 310                 315                 320

Asn Ile Val Lys Pro His Glu Lys Gly Ile Asn Pro Asn Tyr Leu Leu
                325                 330                 335

Ala Trp Lys Gln Val Leu Ala Glu Leu Gln Asp Ile Glu Asn Glu Glu
            340                 345                 350

Lys Ile Pro Lys Thr Lys Asn Met Lys Lys Thr Ser Gln Leu Lys Trp
        355                 360                 365

Ala Leu Gly Glu Asn Met Ala Pro Glu Lys Val Asp Phe Glu Asp Cys
370                 375                 380

Lys Asp Val Ser Asp Leu Lys Gln Tyr Asp Ser Asp Glu Pro Glu Ser
385                 390                 395                 400

Arg Ser Leu Ala Ser Trp Ile Gln Ser Glu Phe Asn Lys Ala Cys Glu
                405                 410                 415

Leu Thr Asp Ser Ser Trp Ile Glu Leu Asp Glu Ile Gly Glu Asp Val
            420                 425                 430

Ala Pro Ile Glu His Ile Ala Ser Met Arg Arg Asn Tyr Phe Thr Ala
        435                 440                 445

Glu Val Ser His Cys Arg Ala Thr Glu Tyr Ile Met Lys Gly Val Tyr
450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495
```

```
Lys Thr Asn Leu Tyr Gly Phe Ile Ile Lys Gly Arg Ser His Leu Arg
                500                 505                 510

Asn Asp Thr Asp Val Val Asn Phe Val Ser Met Glu Phe Ser Leu Thr
            515                 520                 525

Asp Pro Arg Leu Glu Pro His Lys Trp Glu Lys Tyr Cys Val Leu Glu
530                 535                 540

Ile Gly Asp Met Leu Leu Arg Thr Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
            595                 600                 605

Lys Glu Phe Phe Glu Asn Lys Ser Glu Thr Trp Pro Ile Gly Glu Ser
            610                 615                 620

Pro Lys Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
            660                 665                 670

Arg Asp Asn Leu Glu Pro Gly Thr Phe Asp Leu Gly Gly Leu Tyr Glu
            675                 680                 685

Ala Ile Glu Glu Cys Leu Ile Asn Asp Pro Trp Val Leu Leu Asn Ala
690                 695                 700

Ser Trp Phe Asn Ser Phe Leu Thr His Ala Leu Lys
705                 710                 715

<210> SEQ ID NO 5
<211> LENGTH: 2341
<212> TYPE: DNA
<213> ORGANISM: Influenza A virus

<400> SEQUENCE: 5
agcgaaagca ggcaaaccat ttgaatggat gtcaatccga ccttactttt cttgaaagtg    60
ccagcgcaaa atgctataag tactacattc ccttatactg gagatcctcc atacagccat   120
ggaacaggaa caggatacac catggacaca gtcaacagga cacatcaata ctcagaaaag   180
gggaaatgga caacaaacac agagactgga gcaccccaac tcaacccaat tgatggacca   240
ttacctgagg acaacgagcc aagcggatat gcacaaacag attgtgtgtt ggaagcaatg   300
gctttccttg aagaatccca cccagggatc tttgaaaact catgtcttga aacgatggaa   360
gttgttcagc aaacaagagt ggataaactg acccaaggcc gccagactta tgattggaca   420
ttgaatagaa atcagccggc tgcaactgct ttggccaaca ctatagaggt attcagatcg   480
aatggtctaa cagccaatga atcagggagg ctaatagatt ttctcaagga tgtaatggaa   540
tcaatggata aggaagaaat ggaaataaca acacatttcc agagaaagag aagagtaagg   600
gacaacatga ccaagaaaat ggtcacacaa agaacaatag gaagaagaa gcagaggctg   660 aataagagga gctacttaat aagagcactg acactgaaca atgacaaa agatgcagaa   720 agaggcaaat tgaagagacg ggcaattgca cacccggaa tgcagatcag aggattcgtg   780
tactttgtcg aaacattagc gaggagcatc tgcgagaaac ttgagcaatc tggactcccc   840 gttggggga atgagaagaa ggctaaattg gcaaatgtcg tgagaaagat gatgactaac   900
```

-continued

```
tcacaagaca cagagctctc cttcacaatt actggagaca acaccaaatg gaatgagaat    960
cagaaccctc ggatgtttct ggcaatgata acatacatca agaaatca acctgaatgg   1020
tttaggaatg tcttgagcat tgctcctata atgttctcaa acaaaatggc gagattaggg   1080
aaaggttaca tgttcgagag taagagcatg aagctgagga cgcaaatacc agcagaaatg   1140
cttgcaagca ttgacctgaa atacttcaac gaatcaacga ggaagaaaat cgagaaaata   1200
agacctctcc taatagatgg cacagcctca ttgagccctg aatgatgat gggtatgttc   1260
aacatgctga gtacagtctt aggtgtctca atcctgaatc ttgggcaaaa gaggtacacc   1320
aaaaccacat actggtggga tggactccaa tcctctgatg attttgccct catagtgaat   1380
gcaccgaatc atgagggaat acaagcagga gtggataggt tctataggac ctgcaaactg   1440
gttggaatca atatgagcaa gaagaagtct tacataaatc ggacagggac atttgagttc   1500
acaagctttt tctaccgcta tggatttgta gccaatttca gtatggagct gcccagcttt   1560
ggagtgtctg ggataaatga atcggctgac atgagcattg gagttacagt gataaagaac   1620
aatatgataa acaacgatct tggaccagca acagcacaga tggctcttca gctattcatc   1680
aaggactaca ggtacacata ccgatgccac aggggtgata cacaaattca acgaggaga   1740
tcattcgagc tgaagaagtt atgggagcag acccgttcaa aggcaggact attggtttca   1800
gatggaggac caaacctata caatattcgg aatctccaca ttccagaggt ctgcttgaag   1860
tgggaactaa tggatgaaga ttaccagggc aggctgtgta atcctctgaa tccgtttgtc   1920
agtcataaag aaattgaatc cgtaaacaat gctgtggtaa tgccagctca tggtccagcc   1980
aagagcatgg aatatgatgc tgttgcgact acacactcat ggatccctaa gaggaaccgt   2040
tccattctca ataccagcca aggggaatt ctcgaggatg aacagatgta ccagaagtgc   2100
tgcaatctat tcgagaaatt ctttcctagt agttcataca ggaggccagt ggggattcc   2160
agcatggtgg aggccatggt gtctagggcc cgaattgatg cacgaattga cttcgagtct   2220
ggaaggatta agaaagaaga atttgctgag atcatgaaga tctgttccac cattgaggag   2280
ctcagacggc aaaaacagtg aatttggctt gtccttcatg aaaaaatgcc ttgtttctac   2340
t                                                                  2341
```

<210> SEQ ID NO 6
<211> LENGTH: 758
<212> TYPE: PRT
<213> ORGANISM: Influenza A virus

<400> SEQUENCE: 6

```
Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
                20                  25                  30

Gly Thr Gly Thr Gly Tyr Thr Met Asp Thr Val Asn Arg Thr His Gln
            35                  40                  45

Tyr Ser Glu Lys Gly Lys Trp Thr Thr Asn Thr Glu Thr Gly Ala Pro
        50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110
```

-continued

```
Val Val Gln Gln Thr Arg Val Asp Lys Leu Thr Gln Gly Arg Gln Thr
            115                 120                 125

Tyr Asp Trp Thr Leu Asn Arg Asn Gln Pro Ala Ala Thr Ala Leu Ala
130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asp Lys
                165                 170                 175

Glu Glu Met Glu Ile Thr Thr His Phe Gln Arg Lys Arg Arg Val Arg
            180                 185                 190

Asp Asn Met Thr Lys Lys Met Val Thr Gln Arg Thr Ile Gly Lys Lys
            195                 200                 205

Lys Gln Arg Leu Asn Lys Arg Ser Tyr Leu Ile Arg Ala Leu Thr Leu
210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
            275                 280                 285

Met Met Thr Asn Ser Gln Asp Thr Glu Leu Ser Phe Thr Ile Thr Gly
290                 295                 300

Asp Asn Thr Lys Trp Asn Glu Asn Gln Asn Pro Arg Met Phe Leu Ala
305                 310                 315                 320

Met Ile Thr Tyr Ile Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
            355                 360                 365

Pro Ala Glu Met Leu Ala Ser Ile Asp Leu Lys Tyr Phe Asn Glu Ser
370                 375                 380

Thr Arg Lys Lys Ile Glu Lys Ile Arg Pro Leu Leu Ile Asp Gly Thr
385                 390                 395                 400

Ala Ser Leu Ser Pro Gly Met Met Gly Met Phe Asn Met Leu Ser
                405                 410                 415

Thr Val Leu Gly Val Ser Ile Leu Asn Leu Gly Gln Lys Arg Tyr Thr
            420                 425                 430

Lys Thr Thr Tyr Trp Trp Asp Gly Leu Gln Ser Ser Asp Asp Phe Ala
            435                 440                 445

Leu Ile Val Asn Ala Pro Asn His Glu Gly Ile Gln Ala Gly Val Asp
450                 455                 460

Arg Phe Tyr Arg Thr Cys Lys Leu Val Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
            515                 520                 525

Val Ile Lys Asn Asn Met Ile Asn Asn Asp Leu Gly Pro Ala Thr Ala
530                 535                 540
```

```
Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
            565                 570                 575

Lys Lys Leu Trp Glu Gln Thr Arg Ser Lys Ala Gly Leu Leu Val Ser
                580                 585                 590

Asp Gly Gly Pro Asn Leu Tyr Asn Ile Arg Asn Leu His Ile Pro Glu
            595                 600                 605

Val Cys Leu Lys Trp Glu Leu Met Asp Glu Asp Tyr Gln Gly Arg Leu
        610                 615                 620

Cys Asn Pro Leu Asn Pro Phe Val Ser His Lys Glu Ile Glu Ser Val
625                 630                 635                 640

Asn Asn Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Ile Leu Glu Asp Glu Gln Met
        675                 680                 685

Tyr Gln Lys Cys Cys Asn Leu Phe Glu Lys Phe Phe Pro Ser Ser Ser
    690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Ala Glu Ile Met Lys Ile Cys Ser Thr Ile Glu Glu
            740                 745                 750

Leu Arg Arg Gln Lys Gln
        755

<210> SEQ ID NO 7
<211> LENGTH: 2304
<212> TYPE: DNA
<213> ORGANISM: Influenza A virus

<400> SEQUENCE: 7
attcaatatg gagagaataa aagaactaag agatctaatg tcacagtctc gcactcgcga      60
gatactcacc aaaaccactg tggaccacat ggccataatc aaaaagtaca catcaggaag    120
gcaagagaag aaccctgcac tcaggatgaa gtggatgatg gcaatgaaat atccaattac    180
agcagacaag agaataatgg aaatgatccc tgaaaggaat gaacagggac aaacccttg     240 gagcaaaaca aatgatgccg gctcagatcg agtgatggta tcacctctgg ctgtgacatg    300
gtggaatagg aatggaccaa caactagtac agttcattat ccaaaggtgt ataaaactta    360
tttcgaaaaa gtcgaaaggt tgaaacacgg gaccttggc cctgttcact tcagaaatca     420
agttaaaata agacggaggg ttgacataaa ccctggtcac gcagacctca gtgccaaaga    480
ggcacaggat gtaatcatgg aagtcgtttt cccaaatgaa gtgggagcga gaatactaac    540
atcggagtca caactgacga taacaaaaga aagaaggaa gaactccagg actgcaagat    600 tgccccttg atggttgcat acatgttaga aagggagttg gtccgtaaaa cgaggttcct     660
cccagtggct ggtggaacaa gcagtgtcta cattgaggtc tgcatttaa ctcagggac     720 atgctgggag caaatgtaca ccccaggagg ggaagtgagg aatgatgatg ttgaccaaag    780
cttgattatc gctgccagga acatagtaag aagagcaaca gtatcagcag cccactagc    840 atctctattg gagatgtgcc acagcacaca gattggaggg ataaggatgg tagacattct    900
```

-continued

```
tcggcaaaat ccaacagagg aacaagctgt ggacatatgc aaagcagcaa tgggcttaag      960
gattagctca tctttcagct tggcggatt cactttcaaa agaacaagcg ggtcgtcagt      1020
taagagagaa gaagaagtgc ttacgggcaa ccttcaaaca ttgaaaataa gagtacatga      1080
agggtatgaa gagttcacaa tggttgggag aagagcaaca gccattctca ggaaggcaac      1140
cagaagattg atccagctaa tagtaagtgg gagagacgag cagtcaattg ctgaagcaat      1200
aattgtggcc atggtatttt cacaagagga ttgcatgatc aaggcagttc gaggtgattt      1260
gaactttgtc aatagggcaa accagcggct aaacccaatg catcaactct gagacacttt      1320
ccaaaaggat gcaaaagtgc ttttccaaaa ctggggaatt gaacccattg acaatgtaat      1380
gggaatgatc gggatattac ccgacatgac cccaagtact gaaatgtcgc tgaggggggt      1440
aagagtcagt aagatgggag tagatgaata ctccagcaca gagagagtgg tagtgagcat      1500
tgaccgattt ttaagagtcc gggaccaacg ggggaatgtg ctattgtcgc ctgaggaagt      1560
cagcgagaca aagggacag agaagctgac aataacttat tcgtcatcaa tgatgtggga      1620
gatcaatggt cctgaatcgg ttttggtcaa tacttatcag tggatcatca gaaattggga      1680
aactgtgaaa attcaatggt cacaagaccc cacgatgtta taacaaaa tggaattcga      1740 gccatttcag tctctggtcc ctaaggcagc cagaggtcag tacagtggat cgtgaggac      1800 actgttccag cagatgcggg atgtgcttgg aactttcgac actgttcaga ataaaaact      1860 tctccccttt gctgctgctc caccagaaca aagtaggatg caattctcct ccttgactgt      1920
gaatgtgagg ggatcaggaa tgagaatact agtaagggc aattctccag tgttcaacta      1980
caataaggcc actaagaggc ttacagttct cggaaaagat gcaggtgcat tgaccgaaga      2040
tccagatgaa ggcacagctg gagtagagtc tgctgttttg agaggattcc tcatcttggg      2100
caaagaagac aagagatatg gcccagcatt gagcatcaat gagctgagca atcttgcaaa      2160
aggagagaag gctaatgtgc taattgggca aggagacgtg gtgttggtaa tgaaacggaa      2220
acgggactct agcatactta ctgacagcca gacagcgacc aaaagaattc ggatggccat      2280
caattagtgt cgaattgttt aaaa                                            2304
```

<210> SEQ ID NO 8
<211> LENGTH: 759
<212> TYPE: PRT
<213> ORGANISM: Influenza A virus

<400> SEQUENCE: 8

Met Glu Arg Ile Lys Glu Leu Arg Asp Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Met
    50                  55                  60

Glu Met Ile Pro Glu Arg Asn Glu Gln Gly Gln Thr Leu Trp Ser Lys
65                  70                  75                  80

Thr Asn Asp Ala Gly Ser Asp Arg Val Met Val Ser Pro Leu Ala Val
                85                  90                  95

Thr Trp Trp Asn Arg Asn Gly Pro Thr Thr Ser Thr Val His Tyr Pro
            100                 105                 110

Lys Val Tyr Lys Thr Tyr Phe Glu Lys Val Glu Arg Leu Lys His Gly
        115                 120                 125

-continued

Thr Phe Gly Pro Val His Phe Arg Asn Gln Val Lys Ile Arg Arg Arg
    130                 135                 140

Val Asp Ile Asn Pro Gly His Ala Asp Leu Ser Ala Lys Glu Ala Gln
145                 150                 155                 160

Asp Val Ile Met Glu Val Phe Pro Asn Glu Val Gly Ala Arg Ile
                165                 170                 175

Leu Thr Ser Glu Ser Gln Leu Thr Ile Thr Lys Glu Lys Lys Glu Glu
                180                 185                 190

Leu Gln Asp Cys Lys Ile Ala Pro Leu Met Val Ala Tyr Met Leu Glu
            195                 200                 205

Arg Glu Leu Val Arg Lys Thr Arg Phe Leu Pro Val Ala Gly Gly Thr
        210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Val Arg Asn Asp Asp Val Asp
                245                 250                 255

Gln Ser Leu Ile Ile Ala Ala Arg Asn Ile Val Arg Arg Ala Thr Val
            260                 265                 270

Ser Ala Asp Pro Leu Ala Ser Leu Leu Glu Met Cys His Ser Thr Gln
        275                 280                 285

Ile Gly Gly Ile Arg Met Val Asp Ile Leu Arg Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Val Leu Thr Gly Asn Leu Gln Thr Leu
            340                 345                 350

Lys Ile Arg Val His Glu Gly Tyr Glu Glu Phe Thr Met Val Gly Arg
        355                 360                 365

Arg Ala Thr Ala Ile Leu Arg Lys Ala Thr Arg Arg Leu Ile Gln Leu
        370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
                420                 425                 430

Gln Leu Leu Arg His Phe Gln Lys Asp Ala Lys Val Leu Phe Gln Asn
            435                 440                 445

Trp Gly Ile Glu Pro Ile Asp Asn Val Met Gly Met Ile Gly Ile Leu
    450                 455                 460

Pro Asp Met Thr Pro Ser Thr Glu Met Ser Leu Arg Gly Val Arg Val
465                 470                 475                 480

Ser Lys Met Gly Val Asp Glu Tyr Ser Ser Thr Glu Arg Val Val Val
                485                 490                 495

Ser Ile Asp Arg Phe Leu Arg Val Arg Asp Gln Arg Gly Asn Val Leu
            500                 505                 510

Leu Ser Pro Glu Glu Val Ser Glu Thr Gln Gly Thr Glu Lys Leu Thr
        515                 520                 525

Ile Thr Tyr Ser Ser Ser Met Met Trp Glu Ile Asn Gly Pro Glu Ser
    530                 535                 540

Val Leu Val Asn Thr Tyr Gln Trp Ile Ile Arg Asn Trp Glu Thr Val

```
545                 550                 555                 560

Lys Ile Gln Trp Ser Gln Asp Pro Thr Met Leu Tyr Asn Lys Met Glu
                565                 570                 575

Phe Glu Pro Phe Gln Ser Leu Val Pro Lys Ala Ala Arg Gly Gln Tyr
            580                 585                 590

Ser Gly Phe Val Arg Thr Leu Phe Gln Gln Met Arg Asp Val Leu Gly
        595                 600                 605

Thr Phe Asp Thr Val Gln Ile Ile Lys Leu Leu Pro Phe Ala Ala Ala
    610                 615                 620

Pro Pro Glu Gln Ser Arg Met Gln Phe Ser Ser Leu Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Ala Thr Lys Arg Leu Thr Val Leu Gly Lys Asp Ala
            660                 665                 670

Gly Ala Leu Thr Glu Asp Pro Asp Glu Gly Thr Ala Gly Val Glu Ser
        675                 680                 685

Ala Val Leu Arg Gly Phe Leu Ile Leu Gly Lys Glu Asp Lys Arg Tyr
    690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755

<210> SEQ ID NO 9
<211> LENGTH: 1002
<212> TYPE: DNA
<213> ORGANISM: Influenza A virus

<400> SEQUENCE: 9
tagatattga aagatgagtc ttctaaccga ggtcgaaacg tacgttctct ctatcgtccc      60
gtcaggcccc ctcaaagccg agatcgcgca gagacttgaa gatgtctttg caggaaagaa     120
cacagatctt gaagcactca tggaatggct aaagacaaga ccaatcctgt cacctctgac     180
taaggggatt ttaggatttg tgttcacgct caccgtgccc agtgagcgag gactgcagcg     240
tagacgcttt gtccagaatg ctcttaatgg gaatggagat ccaaacaaca tggacagggc     300
agtcaaactg tataggaagc tcaaaaggga aatcacattc catggggcca aagaggtagc     360
actcagttat tccactggtg cacttgccag ttgcatgggc ctcatataca acaggatggg     420
aactgtgacc accgaagtgg catttggcct ggtgtgcgcc acatgtgagc aaattgctga     480
ctcccagcat cggtctcaca ggcagatggt gacaacaacc aacccactga taagacatga     540
gaacaggatg gtactggcta gtaccacggc taaagccatg gagcagatgg cagggtctag     600
cgaacaagca gcagaggcta tggaggttgc cagtcaggct aggcagatgg tgcaggcaat     660
gaggacaatt gggactcatc ctagctccag tgccggtcta aaagatgatc ttcttgaaaa     720
tttgcaggcc taccagaaac ggatgggagt gcaaatgcag cgattcaagt gatcctctcg     780
ttattgcagc aagtatcatt gggatcttgc acttgatatt gtggattctt gatcgtcttt     840
ttttcaaatg cgtttatcgt cgctttaaat acggattgaa aagagggcct tctacggaag     900
gagtgcctga gtctatgagg gaagaatatc ggcaggaaca gcagagtgct gtggatgttg     960
```
acgatggtca ttttgtcaac atagagctgg agtaaaaaac ta                          1002

<210> SEQ ID NO 10
<211> LENGTH: 252
<212> TYPE: PRT
<213> ORGANISM: Influenza A virus

<400> SEQUENCE: 10

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Arg Ala
                85                  90                  95

Val Lys Leu Tyr Arg Lys Leu Lys Arg Glu Ile Thr Phe His Gly Ala
            100                 105                 110

Lys Glu Val Ala Leu Ser Tyr Ser Thr Gly Ala Leu Ala Ser Cys Met
        115                 120                 125

Gly Leu Ile Tyr Asn Arg Met Gly Thr Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Gln
        195                 200                 205

Ala Arg Gln Met Val Gln Ala Met Arg Thr Ile Gly Thr His Pro Ser
    210                 215                 220

Ser Ser Ala Gly Leu Lys Asp Asp Leu Leu Glu Asn Leu Gln Ala Tyr
225                 230                 235                 240

Gln Lys Arg Met Gly Val Gln Met Gln Arg Phe Lys
                245                 250

<210> SEQ ID NO 11
<211> LENGTH: 15
<212> TYPE: PRT
<213> ORGANISM: Influenza A virus

<400> SEQUENCE: 11

Met Ala Ser Gln Gly Thr Lys Arg Ser Tyr Glu Gln Met Glu Thr
1               5                   10                  15

<210> SEQ ID NO 12
<211> LENGTH: 15
<212> TYPE: PRT
<213> ORGANISM: Influenza A virus

<400> SEQUENCE: 12

Gly Ile Gly Arg Phe Tyr Ile Gln Met Cys Thr Glu Leu Lys Leu
1               5                   10                  15

```
<210> SEQ ID NO 13
<211> LENGTH: 11
<212> TYPE: PRT
<213> ORGANISM: Influenza A virus

<400> SEQUENCE: 13

Met Val Leu Ser Ala Phe Asp Glu Arg Arg Asn
1               5                   10

<210> SEQ ID NO 14
<211> LENGTH: 20
<212> TYPE: PRT
<213> ORGANISM: Influenza A virus

<400> SEQUENCE: 14

Tyr Leu Glu Glu His Pro Ser Ala Gly Lys Asp Pro Lys Lys Thr Gly
1               5                   10                  15

Gly Pro Ile Tyr
            20

<210> SEQ ID NO 15
<211> LENGTH: 17
<212> TYPE: PRT
<213> ORGANISM: Influenza A virus

<400> SEQUENCE: 15

Leu Tyr Asp Lys Glu Glu Ile Arg Arg Ile Trp Arg Gln Ala Asn Asn
1               5                   10                  15

Gly

<210> SEQ ID NO 16
<211> LENGTH: 9
<212> TYPE: PRT
<213> ORGANISM: Influenza A virus

<400> SEQUENCE: 16

Ala Thr Tyr Gln Arg Thr Arg Ala Leu
1               5

<210> SEQ ID NO 17
<211> LENGTH: 10
<212> TYPE: PRT
<213> ORGANISM: Influenza A virus

<400> SEQUENCE: 17

Tyr Glu Arg Met Cys Asn Ile Leu Lys Gly
1               5                   10

<210> SEQ ID NO 18
<211> LENGTH: 20
<212> TYPE: PRT
<213> ORGANISM: Influenza A virus

<400> SEQUENCE: 18

Gln Val Arg Glu Ser Arg Asn Pro Gly Asn Ala Glu Ile Glu Asp Leu
1               5                   10                  15

Ile Phe Leu Ala
            20

<210> SEQ ID NO 19
<211> LENGTH: 20
<212> TYPE: PRT
<213> ORGANISM: Influenza A virus
```

```
<400> SEQUENCE: 19

Gln Leu Val Trp Met Ala Cys His Ser Ala Ala Phe Glu Asp Leu Arg
1               5                   10                  15

Val Ser Ser Phe
            20

<210> SEQ ID NO 20
<211> LENGTH: 12
<212> TYPE: PRT
<213> ORGANISM: Influenza A virus

<400> SEQUENCE: 20

Gln Pro Thr Phe Ser Val Gln Arg Asn Leu Pro Phe
1               5                   10

<210> SEQ ID NO 21
<211> LENGTH: 25
<212> TYPE: PRT
<213> ORGANISM: Influenza A virus

<400> SEQUENCE: 21

Lys Ile Glu Thr Asn Lys Phe Ala Ala Ile Cys Thr His Leu Glu Val
1               5                   10                  15

Cys Phe Met Tyr Ser Asp Phe His Phe
            20                  25

<210> SEQ ID NO 22
<211> LENGTH: 11
<212> TYPE: PRT
<213> ORGANISM: Influenza A virus

<400> SEQUENCE: 22

Arg Thr Met Ala Trp Thr Val Val Asn Ser Ile
1               5                   10

<210> SEQ ID NO 23
<211> LENGTH: 11
<212> TYPE: PRT
<213> ORGANISM: Influenza A virus

<400> SEQUENCE: 23

Val Glu Lys Pro Lys Phe Leu Pro Asp Leu Tyr
1               5                   10

<210> SEQ ID NO 24
<211> LENGTH: 12
<212> TYPE: PRT
<213> ORGANISM: Influenza A virus

<400> SEQUENCE: 24

Tyr Tyr Leu Glu Lys Ala Asn Lys Ile Lys Ser Glu
1               5                   10

<210> SEQ ID NO 25
<211> LENGTH: 14
<212> TYPE: PRT
<213> ORGANISM: Influenza A virus

<400> SEQUENCE: 25

Thr His Ile His Ile Phe Ser Phe Thr Gly Glu Glu Met Ala
1               5                   10

<210> SEQ ID NO 26
```

<211> LENGTH: 19
<212> TYPE: PRT
<213> ORGANISM: Influenza A virus

<400> SEQUENCE: 26

Arg Gly Leu Trp Asp Ser Phe Arg Gln Ser Glu Arg Gly Glu Glu Thr
1               5                   10                  15

Ile Glu Glu

<210> SEQ ID NO 27
<211> LENGTH: 15
<212> TYPE: PRT
<213> ORGANISM: Influenza A virus

<400> SEQUENCE: 27

Arg Ser Lys Phe Leu Leu Met Asp Ala Leu Lys Leu Ser Ile Glu
1               5                   10                  15

<210> SEQ ID NO 28
<211> LENGTH: 14
<212> TYPE: PRT
<213> ORGANISM: Influenza A virus

<400> SEQUENCE: 28

His Glu Gly Glu Gly Ile Pro Leu Tyr Asp Ala Ile Lys Cys
1               5                   10

<210> SEQ ID NO 29
<211> LENGTH: 12
<212> TYPE: PRT
<213> ORGANISM: Influenza A virus

<400> SEQUENCE: 29

Ser Gln Leu Lys Trp Ala Leu Gly Glu Asn Met Ala
1               5                   10

<210> SEQ ID NO 30
<211> LENGTH: 14
<212> TYPE: PRT
<213> ORGANISM: Influenza A virus

<400> SEQUENCE: 30

Glu Phe Asn Lys Ala Cys Glu Leu Thr Asp Ser Ser Trp Ile
1               5                   10

<210> SEQ ID NO 31
<211> LENGTH: 15
<212> TYPE: PRT
<213> ORGANISM: Influenza A virus

<400> SEQUENCE: 31

Ser Arg Pro Met Phe Leu Tyr Val Arg Thr Asn Gly Thr Ser Lys
1               5                   10                  15

<210> SEQ ID NO 32
<211> LENGTH: 9
<212> TYPE: PRT
<213> ORGANISM: Influenza A virus

<400> SEQUENCE: 32

Ala Glu Ser Arg Lys Leu Leu Leu Ile
1               5

<210> SEQ ID NO 33
<211> LENGTH: 51

```
<212> TYPE: PRT
<213> ORGANISM: Influenza A virus

<400> SEQUENCE: 33

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu
        50

<210> SEQ ID NO 34
<211> LENGTH: 15
<212> TYPE: PRT
<213> ORGANISM: Influenza A virus

<400> SEQUENCE: 34

Met Ala Phe Leu Glu Glu Ser His Pro Gly Ile Phe Glu Asn Ser
1               5                   10                  15

<210> SEQ ID NO 35
<211> LENGTH: 35
<212> TYPE: PRT
<213> ORGANISM: Influenza A virus

<400> SEQUENCE: 35

Val Gln Gln Thr Arg Val Asp Lys Leu Thr Gln Gly Arg Gln Thr Tyr
1               5                   10                  15

Asp Trp Thr Leu Asn Arg Asn Gln Pro Ala Ala Thr Ala Leu Ala Asn
            20                  25                  30

Thr Ile Glu
        35

<210> SEQ ID NO 36
<211> LENGTH: 14
<212> TYPE: PRT
<213> ORGANISM: Influenza A virus

<400> SEQUENCE: 36

Thr Lys Lys Met Val Thr Gln Arg Thr Ile Gly Lys Lys Lys
1               5                   10

<210> SEQ ID NO 37
<211> LENGTH: 18
<212> TYPE: PRT
<213> ORGANISM: Influenza A virus

<400> SEQUENCE: 37

Phe Val Glu Thr Leu Ala Arg Ser Ile Cys Glu Lys Leu Glu Gln Ser
1               5                   10                  15

Gly Leu

<210> SEQ ID NO 38
<211> LENGTH: 15
<212> TYPE: PRT
<213> ORGANISM: Influenza A virus

<400> SEQUENCE: 38

Arg Met Phe Leu Ala Met Ile Thr Tyr Ile Thr Arg Asn Gln Pro
1               5                   10                  15
```

-continued

<210> SEQ ID NO 39
<211> LENGTH: 38
<212> TYPE: PRT
<213> ORGANISM: Influenza A virus

<400> SEQUENCE: 39

Leu Ser Ile Ala Pro Ile Met Phe Ser Asn Lys Met Ala Arg Leu Gly
1               5                   10                  15

Lys Gly Tyr Met Phe Glu Ser Lys Ser Met Lys Leu Arg Thr Gln Ile
            20                  25                  30

Pro Ala Glu Met Leu Ala
        35

<210> SEQ ID NO 40
<211> LENGTH: 19
<212> TYPE: PRT
<213> ORGANISM: Influenza A virus

<400> SEQUENCE: 40

Ser Pro Gly Met Met Met Gly Met Phe Asn Met Leu Ser Thr Val Leu
1               5                   10                  15

Gly Val Ser

<210> SEQ ID NO 41
<211> LENGTH: 12
<212> TYPE: PRT
<213> ORGANISM: Influenza A virus

<400> SEQUENCE: 41

Gly Ile Asn Met Ser Lys Lys Lys Ser Tyr Ile Asn
1               5                   10

<210> SEQ ID NO 42
<211> LENGTH: 39
<212> TYPE: PRT
<213> ORGANISM: Influenza A virus

<400> SEQUENCE: 42

Thr Gly Thr Phe Glu Phe Thr Ser Phe Phe Tyr Arg Tyr Gly Phe Val
1               5                   10                  15

Ala Asn Phe Ser Met Glu Leu Pro Ser Phe Gly Val Ser Gly Ile Asn
            20                  25                  30

Glu Ser Ala Asp Met Ser Ile
        35

<210> SEQ ID NO 43
<211> LENGTH: 50
<212> TYPE: PRT
<213> ORGANISM: Influenza A virus

<400> SEQUENCE: 43

Gly Val Thr Val Ile Lys Asn Asn Met Ile Asn Asn Asp Leu Gly Pro
1               5                   10                  15

Ala Thr Ala Gln Met Ala Leu Gln Leu Phe Ile Lys Asp Tyr Arg Tyr
            20                  25                  30

Thr Tyr Arg Cys His Arg Gly Asp Thr Gln Ile Gln Thr Arg Arg Ser
        35                  40                  45

Phe Glu
    50

<210> SEQ ID NO 44

```
<211> LENGTH: 9
<212> TYPE: PRT
<213> ORGANISM: Influenza A virus

<400> SEQUENCE: 44

Val Ser Asp Gly Gly Pro Asn Leu Tyr
1               5

<210> SEQ ID NO 45
<211> LENGTH: 12
<212> TYPE: PRT
<213> ORGANISM: Influenza A virus

<400> SEQUENCE: 45

Met Glu Tyr Asp Ala Val Ala Thr Thr His Ser Trp
1               5                   10

<210> SEQ ID NO 46
<211> LENGTH: 23
<212> TYPE: PRT
<213> ORGANISM: Influenza A virus

<400> SEQUENCE: 46

Pro Lys Arg Asn Arg Ser Ile Leu Asn Thr Ser Gln Arg Gly Ile Leu
1               5                   10                  15

Glu Asp Glu Gln Met Tyr Gln
            20

<210> SEQ ID NO 47
<211> LENGTH: 9
<212> TYPE: PRT
<213> ORGANISM: Influenza A virus

<400> SEQUENCE: 47

Ala Glu Ile Met Lys Ile Cys Ser Thr
1               5

<210> SEQ ID NO 48
<211> LENGTH: 34
<212> TYPE: PRT
<213> ORGANISM: Influenza A virus

<400> SEQUENCE: 48

Leu Met Ser Gln Ser Arg Thr Arg Glu Ile Leu Thr Lys Thr Thr Val
1               5                   10                  15

Asp His Met Ala Ile Ile Lys Lys Tyr Thr Ser Gly Arg Gln Glu Lys
            20                  25                  30

Asn Pro

<210> SEQ ID NO 49
<211> LENGTH: 9
<212> TYPE: PRT
<213> ORGANISM: Influenza A virus

<400> SEQUENCE: 49

Trp Met Met Ala Met Lys Tyr Pro Ile
1               5

<210> SEQ ID NO 50
<211> LENGTH: 13
<212> TYPE: PRT
<213> ORGANISM: Influenza A virus

<400> SEQUENCE: 50
```

Pro Glu Arg Asn Glu Gln Gly Gln Thr Leu Trp Ser Lys
1               5                   10

<210> SEQ ID NO 51
<211> LENGTH: 12
<212> TYPE: PRT
<213> ORGANISM: Influenza A virus

<400> SEQUENCE: 51

Pro Leu Ala Val Thr Trp Trp Asn Arg Asn Gly Pro
1               5                   10

<210> SEQ ID NO 52
<211> LENGTH: 13
<212> TYPE: PRT
<213> ORGANISM: Influenza A virus

<400> SEQUENCE: 52

Gly Pro Val His Phe Arg Asn Gln Val Lys Ile Arg Arg
1               5                   10

<210> SEQ ID NO 53
<211> LENGTH: 13
<212> TYPE: PRT
<213> ORGANISM: Influenza A virus

<400> SEQUENCE: 53

Tyr Ile Glu Val Leu His Leu Thr Gln Gly Thr Cys Trp
1               5                   10

<210> SEQ ID NO 54
<211> LENGTH: 10
<212> TYPE: PRT
<213> ORGANISM: Influenza A virus

<400> SEQUENCE: 54

Glu Gln Met Tyr Thr Pro Gly Gly Glu Val
1               5                   10

<210> SEQ ID NO 55
<211> LENGTH: 19
<212> TYPE: PRT
<213> ORGANISM: Influenza A virus

<400> SEQUENCE: 55

Asn Asp Asp Val Asp Gln Ser Leu Ile Ile Ala Ala Arg Asn Ile Val
1               5                   10                  15

Arg Arg Ala

<210> SEQ ID NO 56
<211> LENGTH: 14
<212> TYPE: PRT
<213> ORGANISM: Influenza A virus

<400> SEQUENCE: 56

Ala Ser Leu Leu Glu Met Cys His Ser Thr Gln Ile Gly Gly
1               5                   10

<210> SEQ ID NO 57
<211> LENGTH: 10
<212> TYPE: PRT
<213> ORGANISM: Influenza A virus

<400> SEQUENCE: 57

Ser Phe Ser Phe Gly Gly Phe Thr Phe Lys

```
1               5                   10
```

```
<210> SEQ ID NO 58
<211> LENGTH: 9
<212> TYPE: PRT
<213> ORGANISM: Influenza A virus

<400> SEQUENCE: 58

Leu Thr Gly Asn Leu Gln Thr Leu Lys
1               5

<210> SEQ ID NO 59
<211> LENGTH: 13
<212> TYPE: PRT
<213> ORGANISM: Influenza A virus

<400> SEQUENCE: 59

Arg Val His Glu Gly Tyr Glu Glu Phe Thr Met Val Gly
1               5                   10

<210> SEQ ID NO 60
<211> LENGTH: 12
<212> TYPE: PRT
<213> ORGANISM: Influenza A virus

<400> SEQUENCE: 60

Arg Ala Thr Ala Ile Leu Arg Lys Ala Thr Arg Arg
1               5                   10

<210> SEQ ID NO 61
<211> LENGTH: 11
<212> TYPE: PRT
<213> ORGANISM: Influenza A virus

<400> SEQUENCE: 61

Val Ala Met Val Phe Ser Gln Glu Asp Cys Met
1               5                   10

<210> SEQ ID NO 62
<211> LENGTH: 9
<212> TYPE: PRT
<213> ORGANISM: Influenza A virus

<400> SEQUENCE: 62

Lys Ala Val Arg Gly Asp Leu Asn Phe
1               5

<210> SEQ ID NO 63
<211> LENGTH: 26
<212> TYPE: PRT
<213> ORGANISM: Influenza A virus

<400> SEQUENCE: 63

Val Asn Arg Ala Asn Gln Arg Leu Asn Pro Met His Gln Leu Leu Arg
1               5                   10                  15

His Phe Gln Lys Asp Ala Lys Val Leu Phe
            20                  25

<210> SEQ ID NO 64
<211> LENGTH: 11
<212> TYPE: PRT
<213> ORGANISM: Influenza A virus

<400> SEQUENCE: 64

Arg Val Ser Lys Met Gly Val Asp Glu Tyr Ser
```

-continued

```
<210> SEQ ID NO 65
<211> LENGTH: 15
<212> TYPE: PRT
<213> ORGANISM: Influenza A virus

<400> SEQUENCE: 65

Gly Asn Val Leu Leu Ser Pro Glu Glu Val Ser Glu Thr Gln Gly
1               5                   10                  15

<210> SEQ ID NO 66
<211> LENGTH: 20
<212> TYPE: PRT
<213> ORGANISM: Influenza A virus

<400> SEQUENCE: 66

Leu Thr Ile Thr Tyr Ser Ser Ser Met Met Trp Glu Ile Asn Gly Pro
1               5                   10                  15

Glu Ser Val Leu
            20

<210> SEQ ID NO 67
<211> LENGTH: 11
<212> TYPE: PRT
<213> ORGANISM: Influenza A virus

<400> SEQUENCE: 67

Asn Thr Tyr Gln Trp Ile Ile Arg Asn Trp Glu
1               5                   10

<210> SEQ ID NO 68
<211> LENGTH: 18
<212> TYPE: PRT
<213> ORGANISM: Influenza A virus

<400> SEQUENCE: 68

Met Leu Tyr Asn Lys Met Glu Phe Glu Pro Phe Gln Ser Leu Val Pro
1               5                   10                  15

Lys Ala

<210> SEQ ID NO 69
<211> LENGTH: 20
<212> TYPE: PRT
<213> ORGANISM: Influenza A virus

<400> SEQUENCE: 69

Leu Gly Thr Phe Asp Thr Val Gln Ile Ile Lys Leu Leu Pro Phe Ala
1               5                   10                  15

Ala Ala Pro Pro
            20

<210> SEQ ID NO 70
<211> LENGTH: 32
<212> TYPE: PRT
<213> ORGANISM: Influenza A virus

<400> SEQUENCE: 70

Gln Ser Arg Met Gln Phe Ser Ser Leu Thr Val Asn Val Arg Gly Ser
1               5                   10                  15

Gly Met Arg Ile Leu Val Arg Gly Asn Ser Pro Val Phe Asn Tyr Asn
            20                  25                  30
```

<210> SEQ ID NO 71
<211> LENGTH: 12
<212> TYPE: PRT
<213> ORGANISM: Influenza A virus

<400> SEQUENCE: 71

Gly Val Glu Ser Ala Val Leu Arg Gly Phe Leu Ile
1               5                   10

<210> SEQ ID NO 72
<211> LENGTH: 11
<212> TYPE: PRT
<213> ORGANISM: Influenza A virus

<400> SEQUENCE: 72

Ser Leu Leu Thr Glu Val Glu Thr Tyr Val Leu
1               5                   10

<210> SEQ ID NO 73
<211> LENGTH: 14
<212> TYPE: PRT
<213> ORGANISM: Influenza A virus

<400> SEQUENCE: 73

Lys Thr Arg Pro Ile Leu Ser Pro Leu Thr Lys Gly Ile Leu
1               5                   10

<210> SEQ ID NO 74
<211> LENGTH: 11
<212> TYPE: PRT
<213> ORGANISM: Influenza A virus

<400> SEQUENCE: 74

Gly Phe Val Phe Thr Leu Thr Val Pro Ser Glu
1               5                   10

<210> SEQ ID NO 75
<211> LENGTH: 11
<212> TYPE: PRT
<213> ORGANISM: Influenza A virus

<400> SEQUENCE: 75

Leu Tyr Arg Lys Leu Lys Arg Glu Ile Thr Phe
1               5                   10

<210> SEQ ID NO 76
<211> LENGTH: 10
<212> TYPE: PRT
<213> ORGANISM: Influenza A virus

<400> SEQUENCE: 76

Ala Leu Ala Ser Cys Met Gly Leu Ile Tyr
1               5                   10

<210> SEQ ID NO 77
<211> LENGTH: 15
<212> TYPE: PRT
<213> ORGANISM: Influenza A virus

<400> SEQUENCE: 77

Met Gly Thr Val Thr Thr Glu Val Ala Phe Gly Leu Val Cys Ala
1               5                   10                  15

<210> SEQ ID NO 78
<211> LENGTH: 20
<212> TYPE: PRT

<213> ORGANISM: Influenza A virus

<400> SEQUENCE: 78

Asn Arg Met Val Leu Ala Ser Thr Thr Ala Lys Ala Met Glu Gln Met
1               5                   10                  15

Ala Gly Ser Ser
            20

<210> SEQ ID NO 79
<211> LENGTH: 10
<212> TYPE: PRT
<213> ORGANISM: Influenza A virus

<400> SEQUENCE: 79

Gln Ala Arg Gln Met Val Gln Ala Met Arg
1               5                   10

<210> SEQ ID NO 80
<211> LENGTH: 9
<212> TYPE: PRT
<213> ORGANISM: Influenza A virus

<400> SEQUENCE: 80

Ala Ser Asn Glu Asn Met Glu Thr Met
1               5

<210> SEQ ID NO 81
<211> LENGTH: 10
<212> TYPE: PRT
<213> ORGANISM: Influenza A virus

<400> SEQUENCE: 81

Ser Ser Leu Glu Asn Phe Arg Ala Tyr Val
1               5                   10

<210> SEQ ID NO 82
<211> LENGTH: 15
<212> TYPE: PRT
<213> ORGANISM: Influenza A virus

<400> SEQUENCE: 82

Cys Lys Ile Ala Pro Leu Met Val Ala Tyr Met Leu Glu Arg Glu
1               5                   10                  15

<210> SEQ ID NO 83
<211> LENGTH: 9
<212> TYPE: PRT
<213> ORGANISM: Influenza A virus

<400> SEQUENCE: 83

Ser Ser Tyr Arg Arg Pro Val Gly Ile
1               5

<210> SEQ ID NO 84
<211> LENGTH: 8
<212> TYPE: PRT
<213> ORGANISM: Influenza A virus

<400> SEQUENCE: 84

Met Gly Leu Ile Tyr Asn Arg Met
1               5

INFLUENZA T-CELL IMMUNIZATION AGAINST DIVERSE INFLUENZA A VIRUSES

CROSS-REFERENCE TO RELATED APPLICATIONS

This application claims priority under 35 U.S.C. §119 to Korean Patent Application No. 10-2012-0033317, filed on Mar. 30, 2012, in the Korean Intellectual Property Office, the disclosure of which is incorporated herein by reference in its entirety.

TECHNICAL FIELD

The following disclosure relates to a T cell-based universal influenza vaccine capable of preparing against infection by broad hetero-subtypic influenza viruses and thereby preparing for unpredictable epidemic influenza.

BACKGROUND

Since the 20$^{th}$ century, influenza infectious diseases have claimed a huge number of victims (Nat. Immunol 7,449-455, 2006). Although it has been possible to predict variant viruses that will prevail in the season next year due to the preparation for seasonal influenza by the Global Influenza Surveillance Network (GISN), there still remains uncertainty in that the predicted vaccine strains do not correspond to the epidemic strains of the following year or recombinant vaccine strains are impossible to mass-produce. The epidemic of the Fujian strain from 2003 to 2004, a variant of vaccine strain A/Panama/2007/99, caused the annual average infant mortality rate to rapidly increase from 9 to 153 in the following year (N Engl J Med 350,218-220, 2004). This may be a representative example in which the predicted vaccine candidate strain does not match to the epidemic strain. Unfortunately, the known existing egg-based production process failed to overcome the above disadvantages in the production of influenza vaccine.

The Spanish flu notoriously increased the mortality rate due to unprecedented extreme toxicity. In addition, appearance of highly pathogenic avian influenza (HPAI) H5N1, which has similar pathogenicity to the Spanish flu highlighted the fact that it is very difficult and impossible to prepare for infectious diseases that will prevail in the future (Nature 437, 889-893, 2005). The Global Influenza Surveillance Network (GISN) has conducted epidemiological survey of H5N1 since 2004, and regularly updated the vaccine candidates. Most vaccine manufacturers have developed H5N1 prepandemic vaccine according to the prediction of GISN, and currently, this is the only measure.

The pandemic H1N1 and highly pathogenic avian influenza (HPAI) H5N1 in 2009 caused concerns that highly pathogenic and highly infectious recombinant influenza reassortants might appear in the future. Eventually, only the universal influenza vaccine capable of preventing infection by broad types of viruses would be the ultimate solution. There was a study of proposing a M2 protein as a promising target for universal influenza vaccine (Nat Med 5, 1157-1163, 1999). Since the M2 protein exhibits a significant level of expression on a surface of the cell infected with virus, it can prevent disease or death due to highly pathogenic influenza viruses by using anti-M2 antibodies in cell mediated immunity for removing the cells infected with viruses, but there are some limits therein.

In addition, the combinations of adjuvant agents, virus-like particles (VLP), or inactive seasonal influenza vaccine, for enhancing immunogenicity of M2, are being investigated.

Recently, a highly conserved hemagglutinin (HA) stem region of the influenza virus is drawing attention, and a relatively conserved HA stem is receiving attention as an attractive target capable of neutralizing viruses broadly. Studies about new vaccines against different types of influenza by using these among several groups are being conducted. However, anti-HA stem antibodies have relatively low neutralization activity similarly to the anti-M2 antibodies because they are not direct neutralizing antibodies. Therefore, as long as there are not other defense cooperation means in an antibody-meditated cell immunity aiming on defense, the anti-HA stem antibodies are effective only when the challenge dose is low. Various approaches for T cell-based vaccine have been attempted even though there were no commercially successful cases. Recent studies about HIV and HCV vaccines represented several promising antigen delivery means for inducing broad and active T cell immunity at the time of defense against highly variable viruses. According to the results of study about historical events of the Asian influenza, which was conducted in Cleveland in the year 1957, it can be found that the presence of cross-reactive memory T cells induced by the existing infected viruses has a defense effect even when hetero-subtypic influenza newly prevail. T-cell response has been supposed as a cross defense immune reaction against influenza infection in many clinical researches and animal studies including ferrets and monkeys. The increase in T-cell immunity due to re-infection by hetero-subtypic influenza viruses eventually showed that, the higher the T-cell immunity, the more efficient the defense against highly pathogenic influenza infection. Many research groups have studied antigen delivery methods by highly conserved internal proteins or epitope of influenza virus, such as NP or M1, by using DNA, adenovirus, poxvirus, or live attenuated virus.

Epstein researchers showed that recombinant adenovirus expressing NP and M2 had surprising efficacy in the defense against hetero-subtypic viruses when intranasal administration of vaccine was conducted and a fatal dose of challenge was attempted. T-cell vaccine has an advantage of fast induction for defense immunity, and in particular, the defense immunity is induced in one week after immunization. Many studies have proved that vaccinia virus has promising possibility as a T-cell vaccine vector.

PRIOR ART DOCUMENTS

Non-Patent Documents 1. (Nat Immunol 7,449-455, 2006)
2. (N Engl J Med 350,218-220, 2004)
3. (Nature 437,889-893, 2005)
4. (Nat Med 5, 1157-1163, 1999)

SUMMARY

An embodiment of the present invention is directed to providing a T-cell based universal influenza vaccine containing internal genes allowing broad defense against various hetero-subtypic variants of influenza viruses.

The present invention provides a T-cell based universal influenza vaccine containing internal genes capable of defending broad types of influenza variants in order to prepare for unpredictable epidemic influenza.

Further, the present invention provides a T-cell based universal influenza vaccine containing, as effective components, five kinds of internal genes, NP (SEQ ID NO: 1), PA (SEQ ID NO: 3), PB1 (SEQ ID NO: 5), PB2 (SEQ ID NO: 7), and M1 (SEQ ID NO: 9), which have a consensus sequence and are selected from the bird, pig, and human influenza isolates. An aspect of the present invention provides a T-cell based universal influenza vaccine containing, as effective components, NP (SEQ ID NO: 1) and PA (SEQ ID NO: 3) genes. Another aspect of the present invention provides a T-cell based universal influenza vaccine containing, as effective components, NP (SEQ ID NO: 1) and PA (SEQ ID NO: 3) genes, and further containing, as another effective component, at least one selected from PB1 (SEQ ID NO: 5), PB2 (SEQ ID NO: 7), and M1 (SEQ ID NO: 9) genes. Still another aspect of the present invention provides a T-cell based universal influenza vaccine containing all of NP (SEQ ID NO: 1), PA (SEQ ID NO: 3), PB1 (SEQ ID NO: 5), PB2 (SEQ ID NO: 7), and M1 (SEQ ID NO: 9) genes.

In addition, in the T-cell based universal influenza vaccine: a CTL epitope of the NP gene has a sequence consisting of:

```
                                          (SEQ ID NO: 11)
 1. MASQGTKRSYEQMET, (SEQ ID NO: 12)
 2. GIGRFYIQMCTELKL, (SEQ ID NO: 13)
 3. MVLSAFDERRN, (SEQ ID NO: 14)
 4. YLEEHPSAGKDPKKTGGPIY, (SEQ ID NO: 15)
 5. LYDKEEIRRIWRQANNG, (SEQ ID NO: 16)
 6. ATYQRTRAL, (SEQ ID NO: 17)
 7. YERMCNILKG, (SEQ ID NO: 18)
 8. QVRESRNPGNAEIEDLIFLA, (SEQ ID NO: 19)
 9. QLVWMACHSAAFEDLRVSSF,
or
                                          (SEQ ID NO: 20)
10. QPTFSVQRNLPF;
``` a CTL epitope of the PA gene has a sequence consisting of:

```
                                          (SEQ ID NO: 21)
 1. KIETNKFAAICTHLEVCFMYSDFHF, (SEQ ID NO: 22)
 2. RTMAWTVVNSI, (SEQ ID NO: 23)
 3. VEKPKFLPDLY, (SEQ ID NO: 24)
 4. YYLEKANKIKSE, (SEQ ID NO: 25)
 5. THIHIFSFTGEEMA, (SEQ ID NO: 26)
 6. RGLWDSFRQSERGEETIEE, (SEQ ID NO: 27)
 7. RSKFLLMDALKLSIE, (SEQ ID NO: 28)
 8. HEGEGIPLYDAIKC, (SEQ ID NO: 29)
 9. SQLKWALGENMA, (SEQ ID NO: 30)
10. EFNKACELTDSSWI, (SEQ ID NO: 31)
11. SRPMFLYVRTNGTSK,
or
                                          (SEQ ID NO: 32)
12. AESRKLLLI;
``` a CTL epitope of the PB1 gene has a sequence consisting of:

```
                                          (SEQ ID NO: 33)
 1. MDVNPTLLFLKVPAQNAISTTFPYTGDPPYSHGTGTGYTMDTVNRTHQYSE, (SEQ ID NO: 34)
 2. MAFLEESHPGIFENS, (SEQ ID NO: 35)
 3. VQQTRVDKLTQGRQTYDWTLNRNQPAATALANTIE, (SEQ ID NO: 36)
 4. TKKMVTQRTIGKKK, (SEQ ID NO: 37)
 5. FVETLARSICEKLEQSGL, (SEQ ID NO: 38)
 6. RMFLAMITYITRNQP, (SEQ ID NO: 39)
 7. LSIAPIMFSNKMARLGKGYMFESKSMKLRTQIPAEMLA, (SEQ ID NO: 40)
 8. SPGMMMGMFNMLSTVLGVS, (SEQ ID NO: 41)
 9. GINMSKKKSYIN, (SEQ ID NO: 42)
10. TGTFEFTSFFYRYGFVANFSMELPSFGVSGINESADMSI, (SEQ ID NO: 43)
11. GVTVIKNNMINNDLGPATAQMALQLFIKDYRYTYRCHRGDTQIQTRRSFE,
```

-continued

12. VSDGGPNLY, (SEQ ID NO: 44)

13. MEYDAVATTHSW, (SEQ ID NO: 45)

14. PKRNRSILNTSQRGILEDEQMYQ, (SEQ ID NO: 46)
or

15. AEIMKICST; (SEQ ID NO: 47)

a CTL epitope of the PB2 gene has a sequence consisting of:

1. LMSQSRTREILTKTTVDHMAIIKKYTSGRQEKNP, (SEQ ID NO: 48)

2. WMMAMKYPI, (SEQ ID NO: 49)

3. PERNEQGQTLWSK, (SEQ ID NO: 50)

4. PLAVTWWNRNGP, (SEQ ID NO: 51)

5. GPVHFRNQVKIRR, (SEQ ID NO: 52)

6. YIEVLHLTQGTCW, (SEQ ID NO: 53)

7. EQMYTPGGEV, (SEQ ID NO: 54)

8. NDDVDQSLIIAARNIVRRA, (SEQ ID NO: 55)

9. ASLLEMCHSTQIGG, (SEQ ID NO: 56)

10. SFSFGGFTFK, (SEQ ID NO: 57)

11. LTGNLQTLK, (SEQ ID NO: 58)

12. RVHEGYEEFTMVG, (SEQ ID NO: 59)

13. RATAILRKATRR, (SEQ ID NO: 60)

14. VAMVFSQEDCM, (SEQ ID NO: 61)

15. KAVRGDLNF, (SEQ ID NO: 62)

16. VNRANQRLNPMHQLLRHFQKDAKVLF, (SEQ ID NO: 63)

17. RVSKMGVDEYS, (SEQ ID NO: 64)

18. GNVLLSPEEVSETQG, (SEQ ID NO: 65)

19. LTITYSSSMMWEINGPESVL, (SEQ ID NO: 66)

20. NTYQWIIRNWE, (SEQ ID NO: 67)

21. MLYNKMEFEPFQSLVPKA, (SEQ ID NO: 68)

-continued

22. LGTFDTVQIIKLLPFAAAPP, (SEQ ID NO: 69)

23. QSRMQFSSLTVNVRGSGMRILVRGNSPVFNYN, (SEQ ID NO: 70)
or

24. GVESAVLRGFLI; (SEQ ID NO: 71)
and a CTL epitope of the M1 gene has a sequence consisting of:

1. SLLTEVETYVL, (SEQ ID NO: 72)

2. KTRPILSPLTKGIL, (SEQ ID NO: 73)

3. GFVFTLTVPSE, (SEQ ID NO: 74)

4. LYRKLKREITF, (SEQ ID NO: 75)

5. ALASCMGLIY, (SEQ ID NO: 76)

6. MGTVTTEVAFGLVCA, (SEQ ID NO: 77)

7. NRMVLASTTAKAMEQMAGSS, (SEQ ID NO: 78)
or

8. QARQMVQAMR. (SEQ ID NO: 79)

Therefore, the NP (SEQ ID NO: 1), PA (SEQ ID NO: 3), PB1 (SEQ ID NO: 5), PB2 (SEQ ID NO: 7), and M1 (SEQ ID NO: 9) genes each are characterized by containing at least one CTL epitope.

Preferably, a T-cell vaccine delivery vector may include a recombinant virus, and the recombinant virus is selected from recombinant vaccinia virus, recombinant adenovirus, recombinant adeno associated virus, recombinant retrovirus, and recombinant lentivirus. More preferably, the recombinant (replicating) vaccinia virus (hereinafter, referred to as 'rVV') may be used.

The administration route of the vaccine according to the present invention may be a skin scarification (s.s.), intramuscular (i.m.), intranasal (i.n.), intradermal (i.d.), intravenous (i.v.), or intraperitoneal (i.p.) route, but is not limited thereto. An administration method using the skin scarification (s.s.) route is most preferable.

The T-cell based universal influenza vaccine of the present invention may include at least one additive selected from pharmaceutically acceptable immunopotentiator, carrier, excipient, and diluent, and may be provided in a unit-dose container or a multi-dose container, for example, sealed ample, bottle, or the like.

BRIEF DESCRIPTION OF THE DRAWINGS

FIG. 2 shows a graph depicting the effect according to the administration method of rVV-NP immunization by using IFN-γ-ELISPOT activity.

$10^6$ pfu of rVV-NP vaccine was administered to the C57BL/6 mice through the intramuscular (i.m), intranasal (i.n.), or skin scarification (s.s.) route. The splenocytes stimulated with $NP_{366}$ CTL epitope peptides after 10 days or 4 weeks of immunization were analyzed by IFN-γ-ELISPOT assay (each bar indicates average±standard deviation (SD) for 2 mice/group.

FIG. 3 shows a graph depicting the effect according to the vaccination administration method of x-31 by using IFN-γ-ELISPOT activity. C57BL/6 mice were vaccinated with $10^4$ pfu of x-31 through the combination of intramuscular (i.m) and intranasal (i.n.) routes two times at an interval of 4 weeks, without anesthesia. The splenocytes stimulated with by $NP_{366}$ CTL epitope peptides after 10 days of vaccination were analyzed by IFN-γ-ELISPOT assay (each bar indicates average±standard deviation (SD) for 2 mice/group.

Figure 4A:
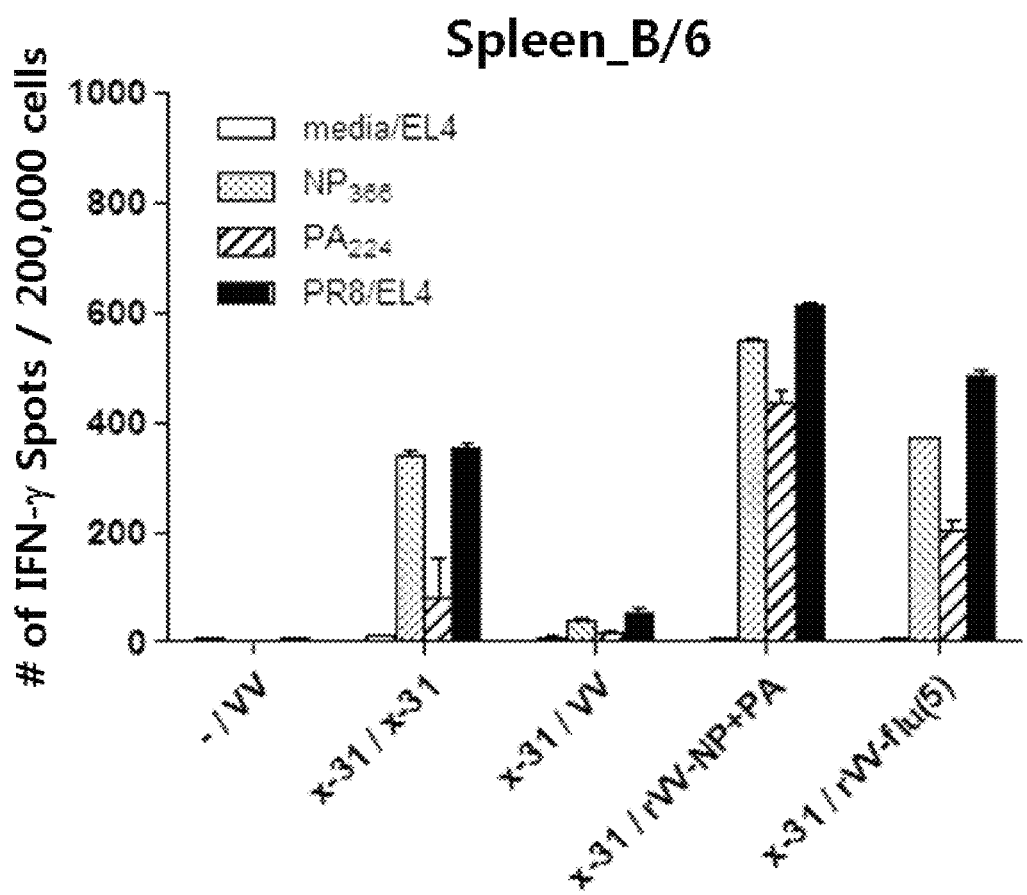

FIG. 4A shows a graph depicting the influenza-specific T-cell response induced by rVV-flu vaccination route in x-31-prime-immunized mice. x-31-primed C57BL/6 mice were challenged with $10^6$ pfu of vaccinia influenza. rVV-flu (5) is vaccine consisting of rVV-NP, -PA, -M1, -PB2, and -PB1, and parental vaccinia (VV) or x-31 is a control. FIG. 4A shows evaluation of IFN-γ-ELISPOT activity in splenocytes stimulated with $NP_{366}$ or $PA_{224}$ epitope or PR8-infected EL4 cells after 3 weeks of immunization in C57BL/6 mice.

Figure 4B:
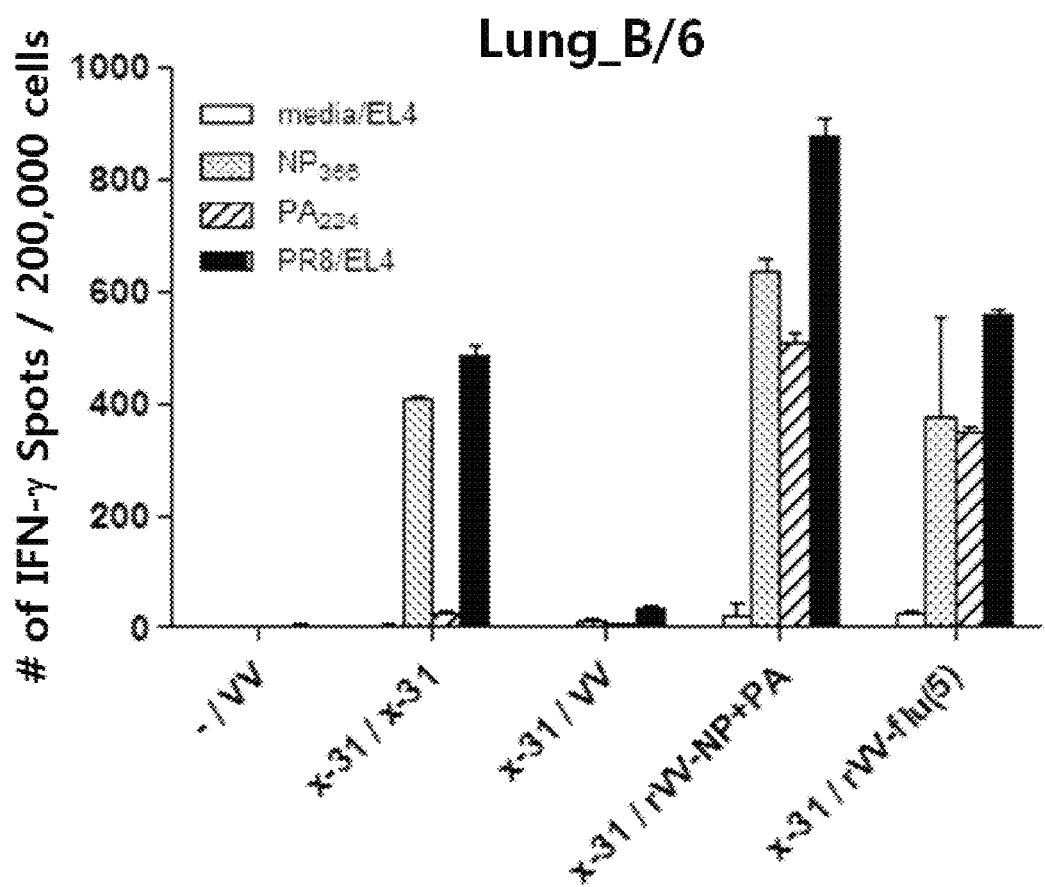

FIG. 4B shows a graph depicting the influenza-specific T-cell response induced by rVV-flu vaccination route in x-31-prime-immunized mice. x-31-primed C57BL/6 mice were challenged with $10^6$ pfu of vaccinia influenza. rVV-flu (5) is vaccine consisting of rVV-NP, -PA, -M1, -PB2, and -PB1, and parental vaccinia (VV) or x-31 is a control. FIG. 4B shows evaluation of IFN-γ-ELISPOT activity in lung cells stimulated with $NP_{366}$ or $PA_{224}$ epitope or PR8-infected EL4 cells after 3 weeks of immunization in C57BL/6 mice.

FIG. 4C shows a graph depicting the influenza-specific T-cell response induced by rVV-flu vaccination route in x-31-prime-immunized mice. x-31-primed C57BL/6 mice were challenged with $10^6$ pfu of vaccinia influenza. rVV-flu (5) is vaccine consisting of rVV-NP, -PA, -M1, -PB2, and -PB1, and parental vaccinia (VV) or x-31 is a control. FIG. 4C shows functional lytic activity by in vivo CTL assay, on day 7 after immunization (each bar indicates average±standard deviation (SD) for 2~3 mice/group).

FIG. 4D shows a graph depicting the influenza-specific T-cell response induced by rVV-flu vaccination route in x-31-prime-immunized mice. Balb/c mice were challenged with $10^6$ pfu of vaccinia influenza. rVV-flu (5) is vaccine consisting of rVV-NP, -PA, -M1, -PB2, and -PB1, and parental vaccinia (VV) or x-31 is a control. FIG. 4D shows evaluation of IFN-γ-ELISPOT activity in splenocytes stimulated with $NP_{147}$ epitope after 3 weeks of immunization in Balb/c mice.

Figure 4E:
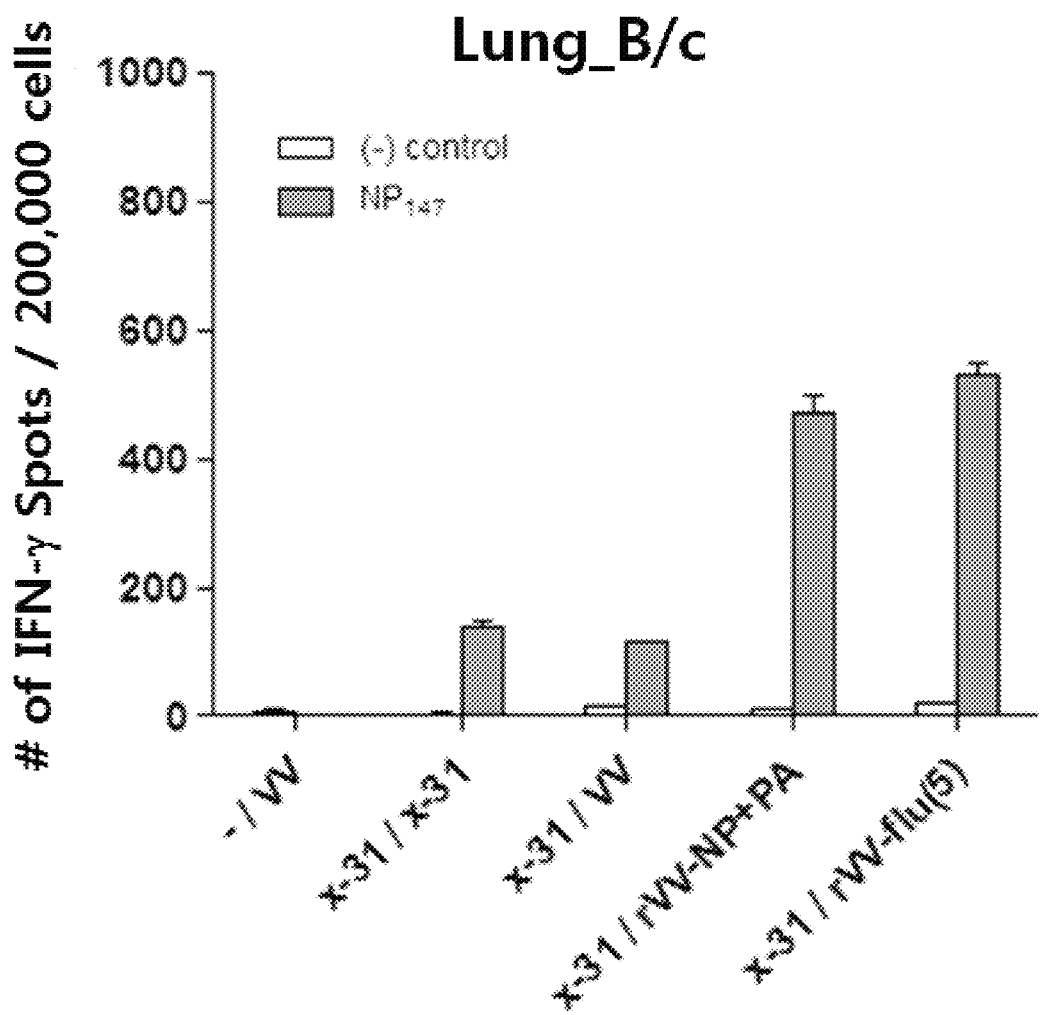

FIG. 4E shows a graph depicting the influenza-specific T-cell response induced by rVV-flu vaccination route in x-31-prime-immunized mice. Balb/c mice were challenged with $10^6$ pfu of vaccinia influenza. rVV-flu (5) is vaccine consisting of rVV-NP, -PA, -M1, -PB2, and -PB1, and parental vaccinia (VV) or x-31 is a control. FIG. 4E shows evaluation of IFN-γ-ELISPOT activity in lung cells stimulated with $NP_{147}$ epitope after 3 weeks of immunization in Balb/c mice.

Figure 4F:
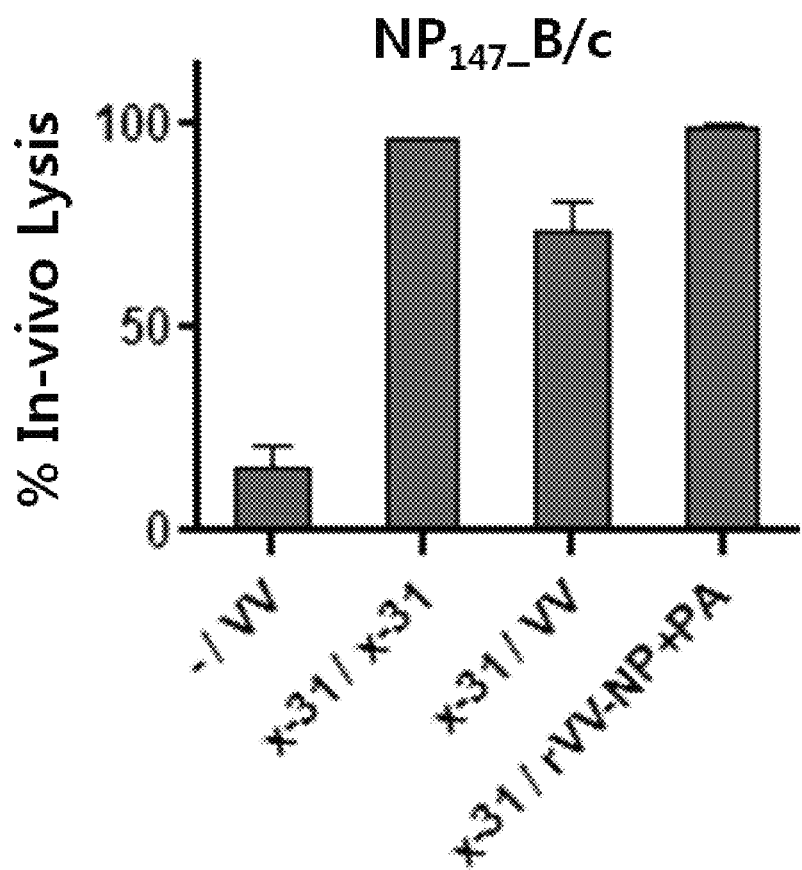

FIG. 4F shows a graph depicting the influenza-specific T-cell response induced by rVV-flu vaccination route in x-31-prime-immunized mice. Balb/c mice were challenged with $10^6$ pfu of vaccinia influenza. rVV-flu (5) is vaccine consisting of rVV-NP, -PA, -M1, -PB2, and -PB1, and parental vaccinia (VV) or x-31 is a control. FIG. 4F shows functional lytic activity by in vivo CTL assay, on day 7 after immunization (each bar indicates average±standard deviation (SD) for 2~3 mice/group).

Figure 5A:
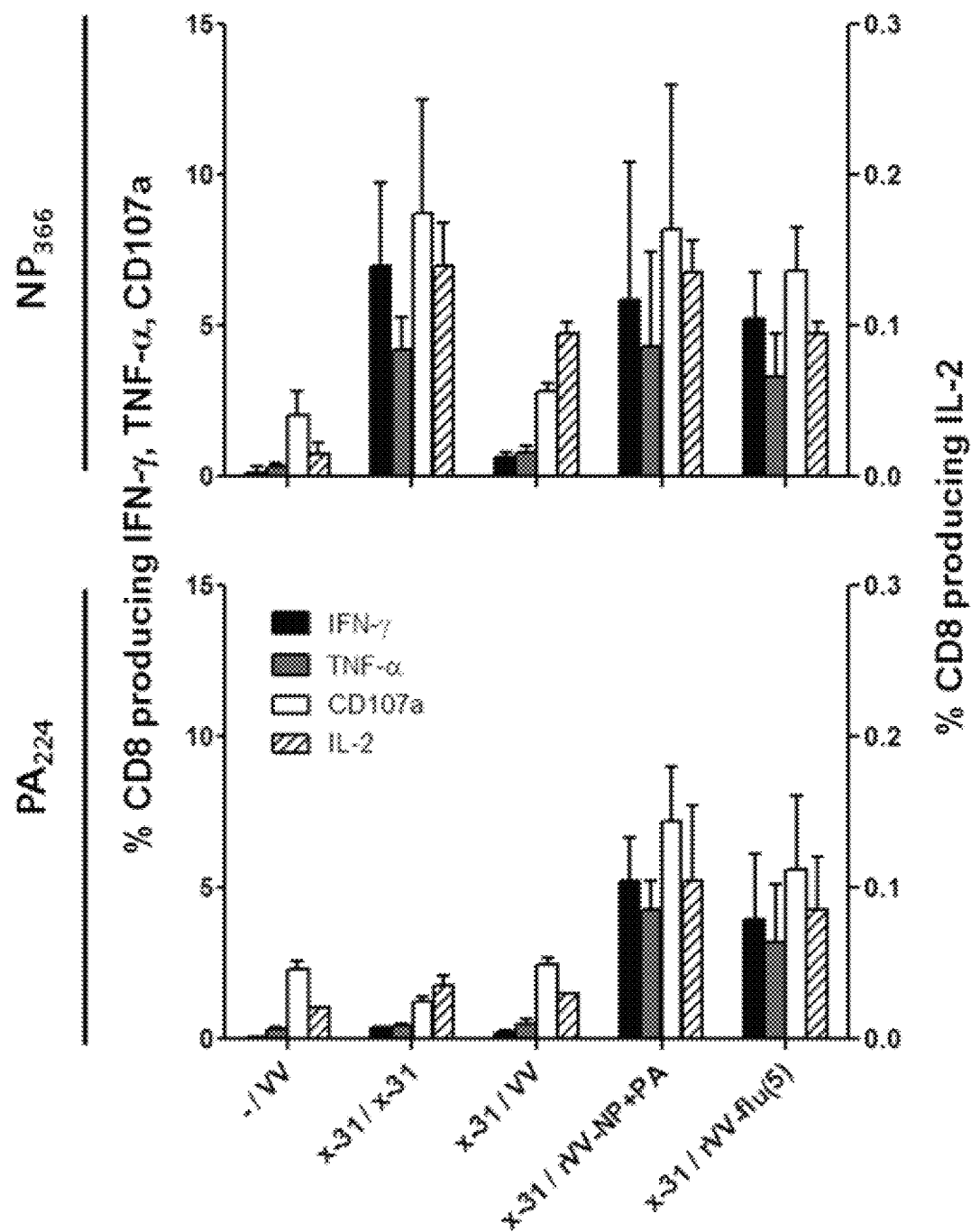

FIG. 5A shows a graph depicting secretion of multifunctional cytokine from influenza-specific T-cells. The splenocytes of C57BL/6 mice were used, and stimulated with $NP_{366}$ (upper panel) or $PA_{224}$ (lower panel) epitopes after 7 weeks of rVV-flu immunization. Secretion of IFN-γ, TNF-α and IL-2 cytokines and expression of degranulation marker (CD107a) were measured by in vivo cytokine staining: FIG. 5A shows the rate (%) of CD8 T-cells secreted by each cytokine.

Figure 5B:
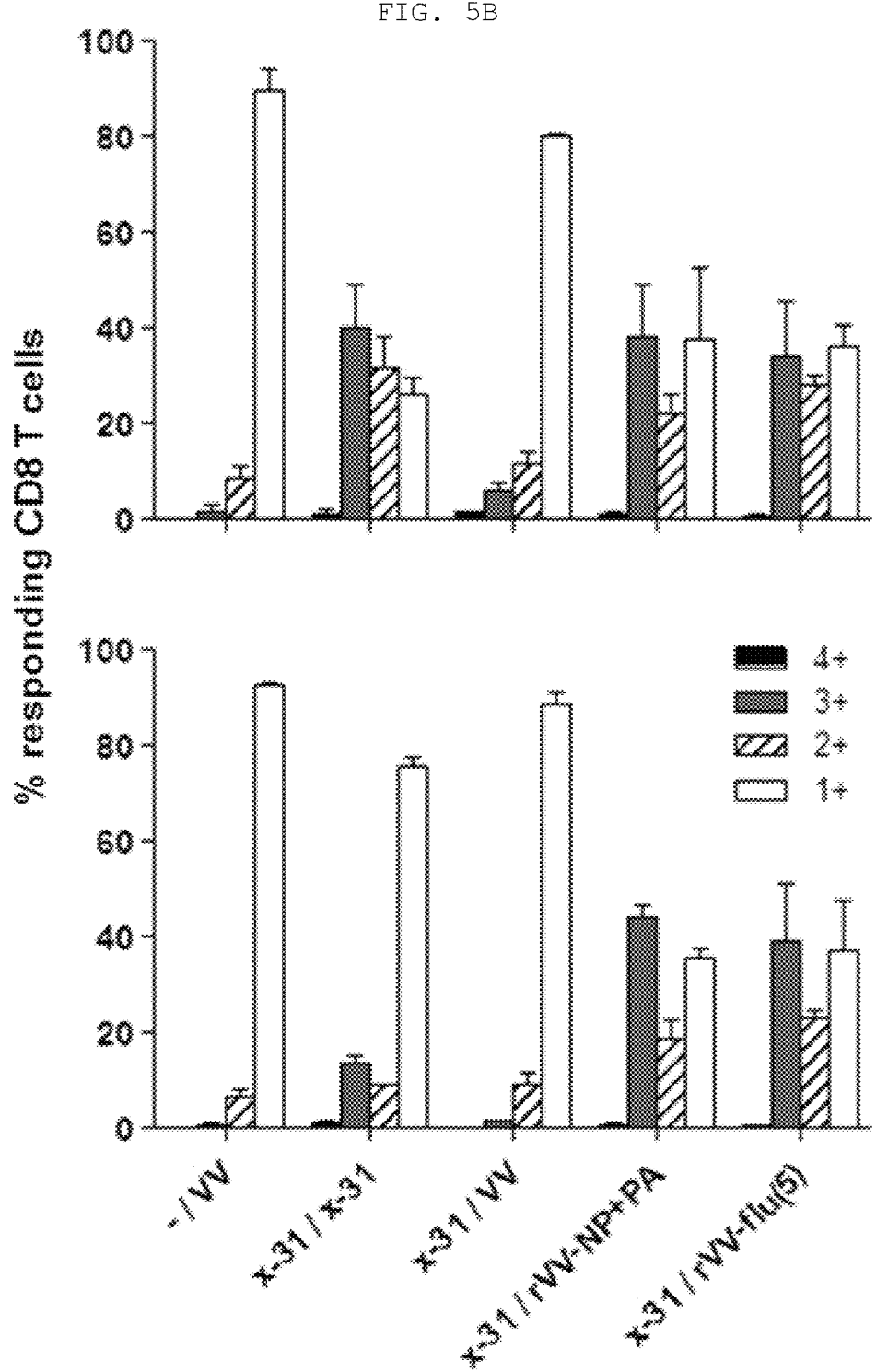

FIG. 5B shows a graph depicting secretion of multifunctional cytokine from influenza-specific T-cells. The splenocytes of C57BL/6 mice were used, and stimulated with $NP_{366}$ (upper panel) or $PA_{224}$ (lower panel) epitopes after 7 weeks of rVV-flu immunization. Secretion of IFN-γ, TNF-α and IL-2 cytokines and expression of degranulation marker (CD107a) were measured by in vivo cytokine staining: FIG. 5B shows measurement results of T-cell response and degranulation for various cytokine combinations in order to analyze multi-functionality of the influenza-specific T-cells (each bar indicates average±standard deviation (SD) for 2 mice/group).

Figure 5C:
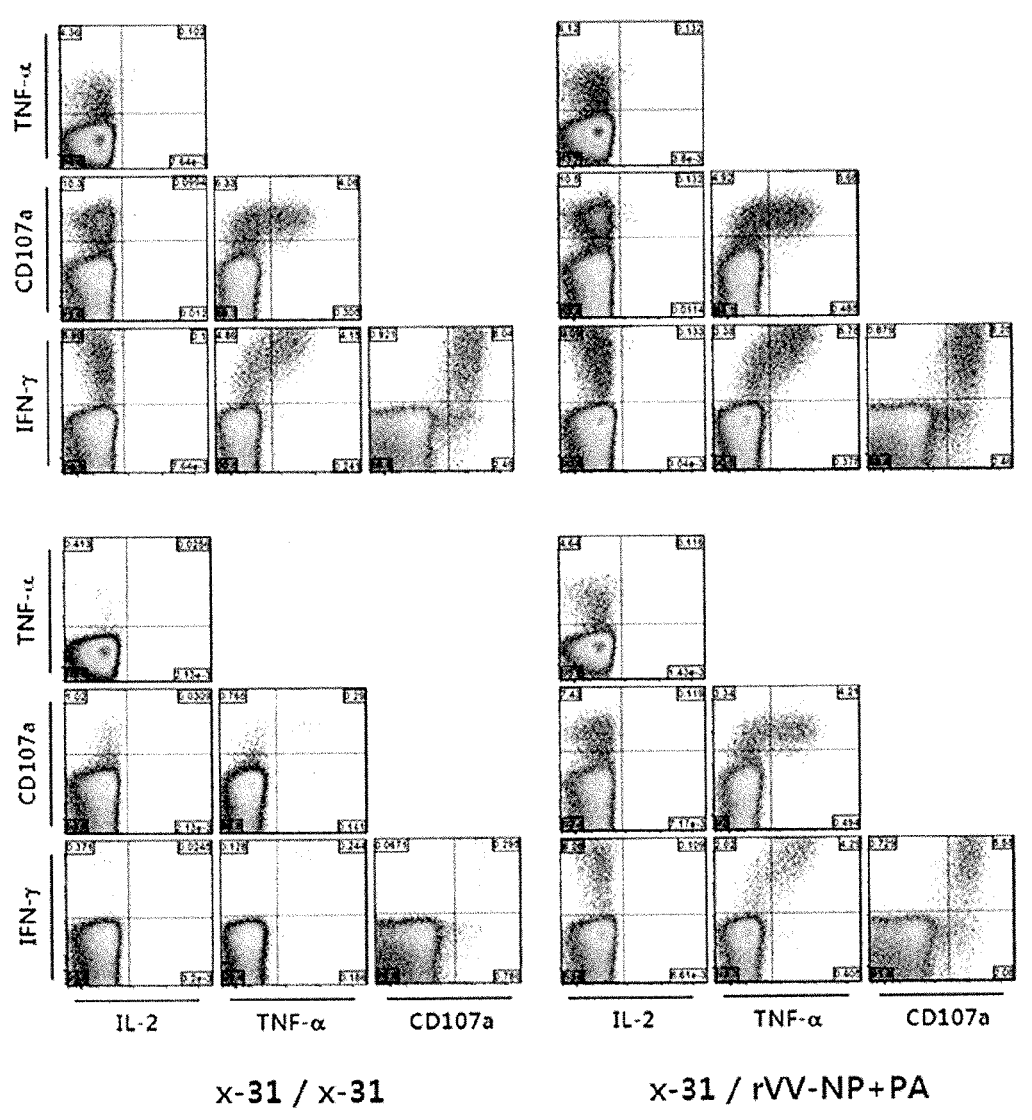

FIG. 5C shows a graph depicting secretion of multifunctional cytokine from influenza-specific T-cells. The splenocytes of C57BL/6 mice were used, and stimulated with $NP_{366}$ (upper panel) or $PA_{224}$ (lower panel) epitopes after 7 weeks of rVV-flu immunization. Secretion of IFN-γ, TNF-α and IL-2 cytokines and expression of degranulation marker (CD107a) were measured by in vivo cytokine staining: FIG. 5C shows dot plots for a positive (+) control and rVV-NP+PA.

Figure 6:
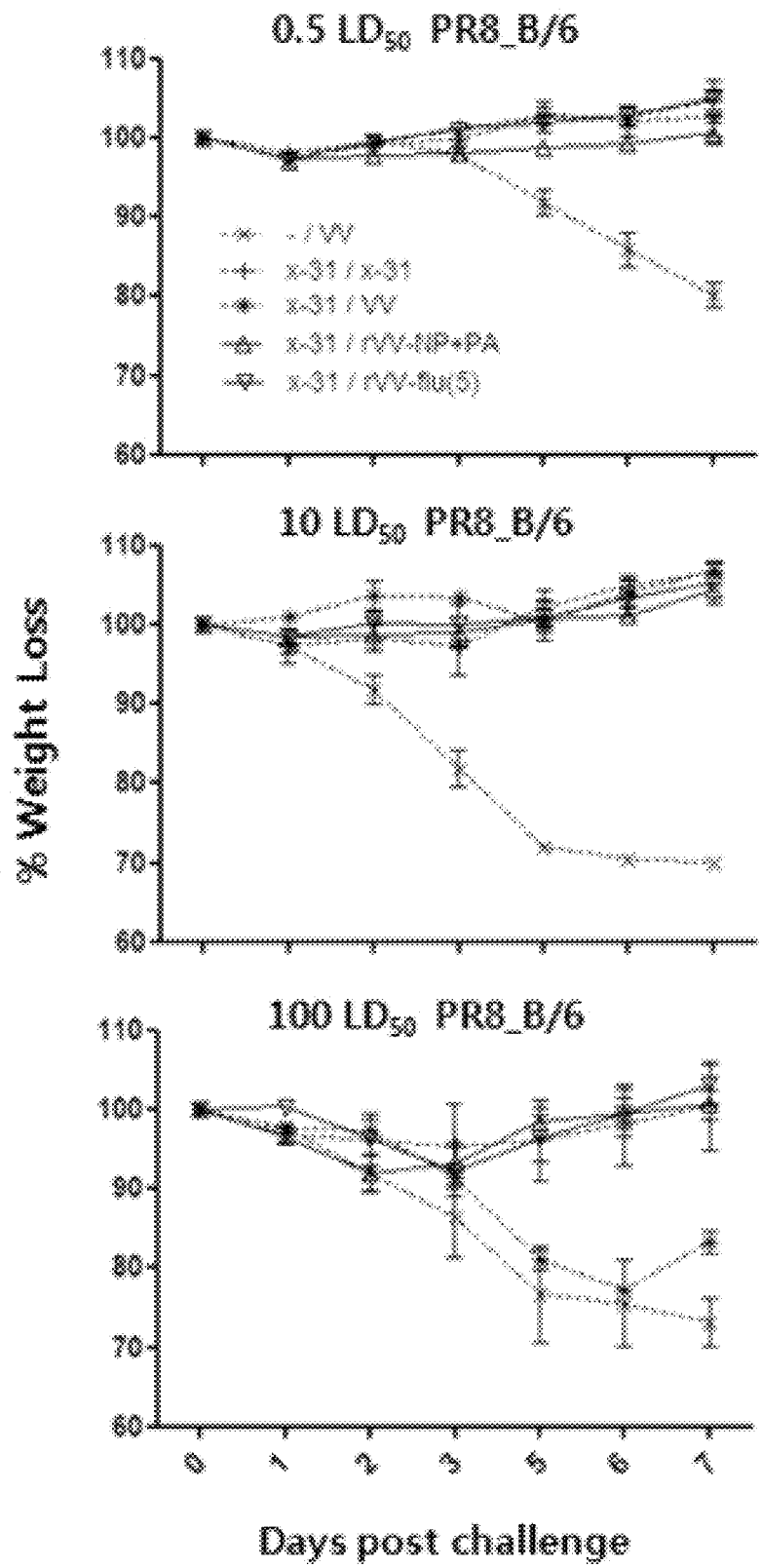

FIG. 6 shows a graph depicting weight loss for 7 days when C57BL/6 mice were challenged with PR8 ($0.5/1_0/10_0 _LD_{50}$), after immunization (each bar indicates average±standard error of measurement (SEM) for 4 mice/group).

Figure 7A:
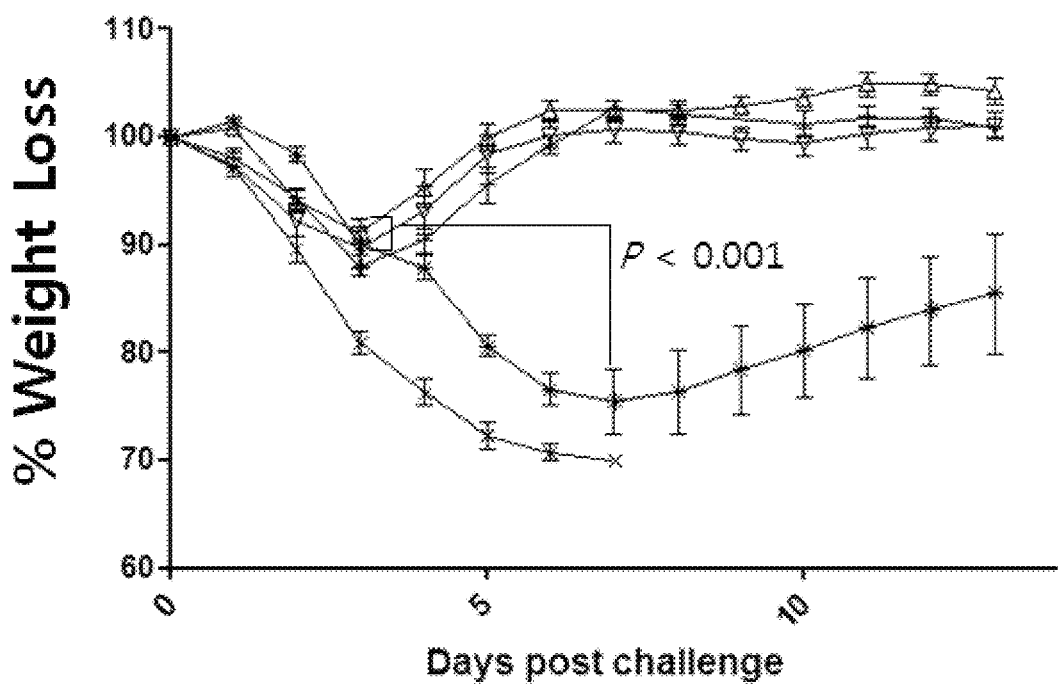

FIG. 7A shows graph depicting weight loss and survival rate when x-31-prime-immunized C57BL/6 mice were challenged with PR8 (100 $LD_{50}$), after 3 weeks of rVV-flu immunization. The % weight loss were tracked for 2 weeks (each bar indicates average±standard error of measurement (SEM) for 8 mice/group.

Figure 7B:
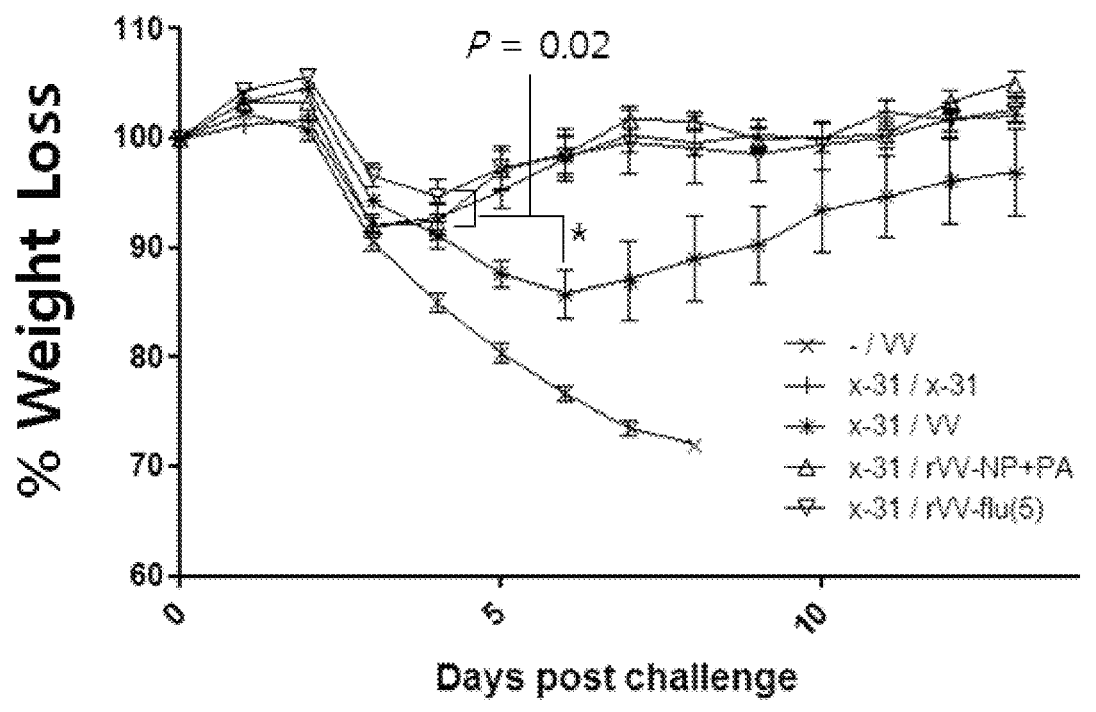

FIG. 7B shows graph depicting weight loss and survival rate when x-31-prime-immunized Balb/mice were challenged with PR8 (100 $LD_{50}$), after 3 weeks of rVV-flu immunization. The % weight loss were tracked for 2 weeks (each bar indicates average±standard error of measurement (SEM) for 8 mice/group).

Figure 7C:
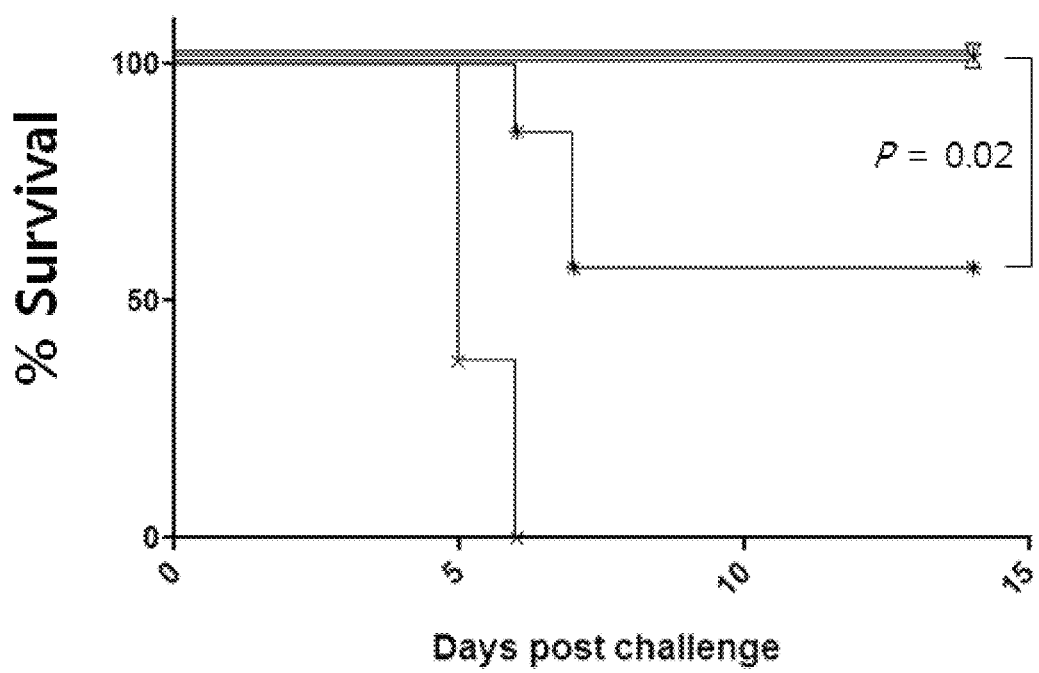

FIG. 7C shows graph depicting weight loss and survival rate when x-31-prime-immunized C57BL/6 mice were challenged with PR8 (100 $LD_{50}$), after 3 weeks of rVV-flu immunization. The % survival were tracked for 2 weeks (each bar indicates average±standard error of measurement (SEM) for 8 mice/group.

FIG. 7D shows a graph depicting weight loss and survival rate when x-31-prime-immunized Balb/c mice were challenged with PR8 (100 $LD_{50}$), after 3 weeks of rVV-flu immunization. The % survival were tracked for 2 weeks (each bar indicates average±standard error of measurement (SEM) for 8 mice/group).

Figure 7E:
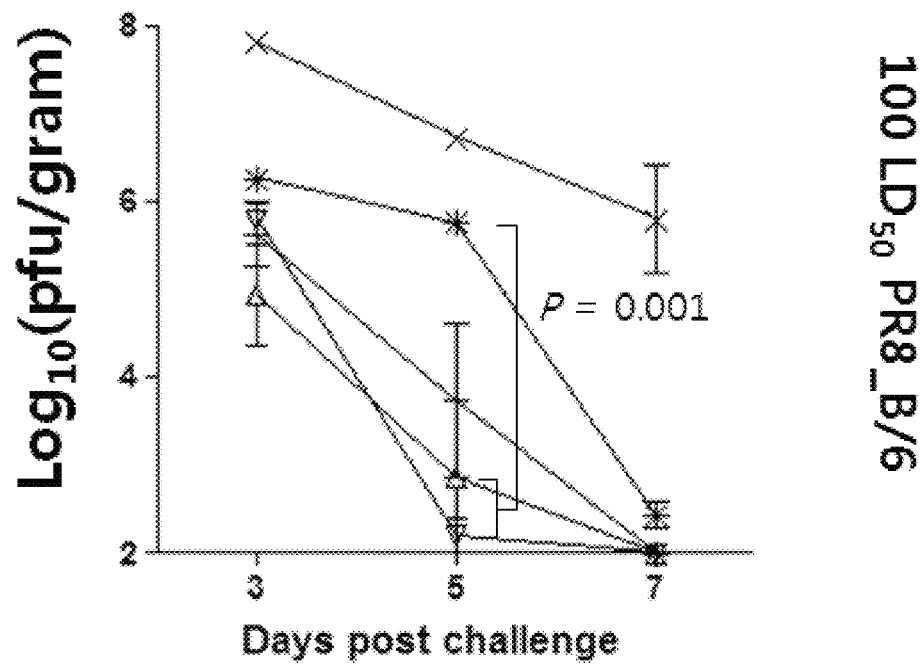

FIG. 7E shows a graph depicting weight loss and survival rate when x-31-prime-immunized C57BL/6 and Balb/c mice were challenged with PR8 (100 $LD_{50}$), after 3 weeks of rVV-flu immunization. Lung virus titers were measured on day 3, 5, and 7 post challenge (each bar indicates average±standard error of measurement (SEM) for 3 mice/group).

Figure 7F:
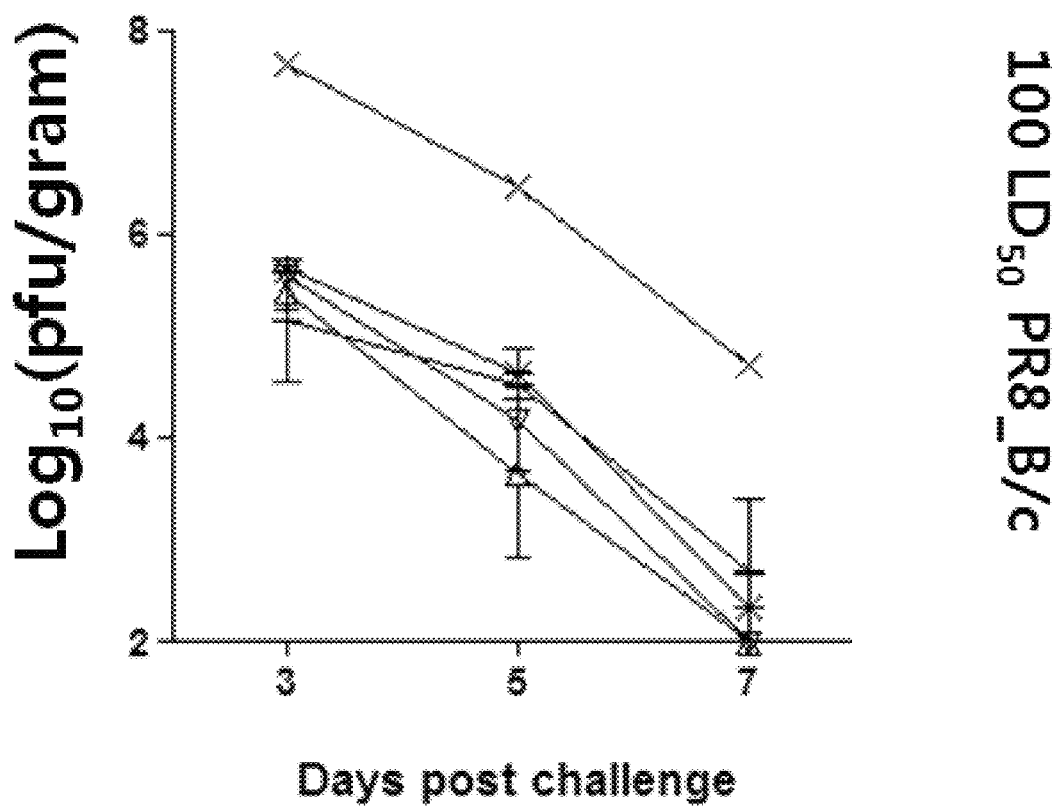

FIG. 7F shows a graph depicting weight loss and survival rate when x-31-prime-immunized C57BL/6 and Balb/c mice were challenged with PR8 (100 $LD_{50}$), after 3 weeks of rVV-flu immunization. Lung virus titers were measured on day 3, 5, and 7 post challenge (each bar indicates average±standard error of measurement (SEM) for 3 mice/group).

FIG. 8A shows a graph depicting the weight loss and survival rate of x-31-prime-immunized C57BL/6 mice, which were challenged with HPAI H5N1 after 3 weeks of rVV-flu immunization (100 $LD_{50}$ A/MD/W401/11 (HPAI H5N1 field isolate)). The % weight loss were tracked for 2 weeks (each bar indicates average±standard error of measurement (SEM) for 8 mice/group).

Figure 8B:
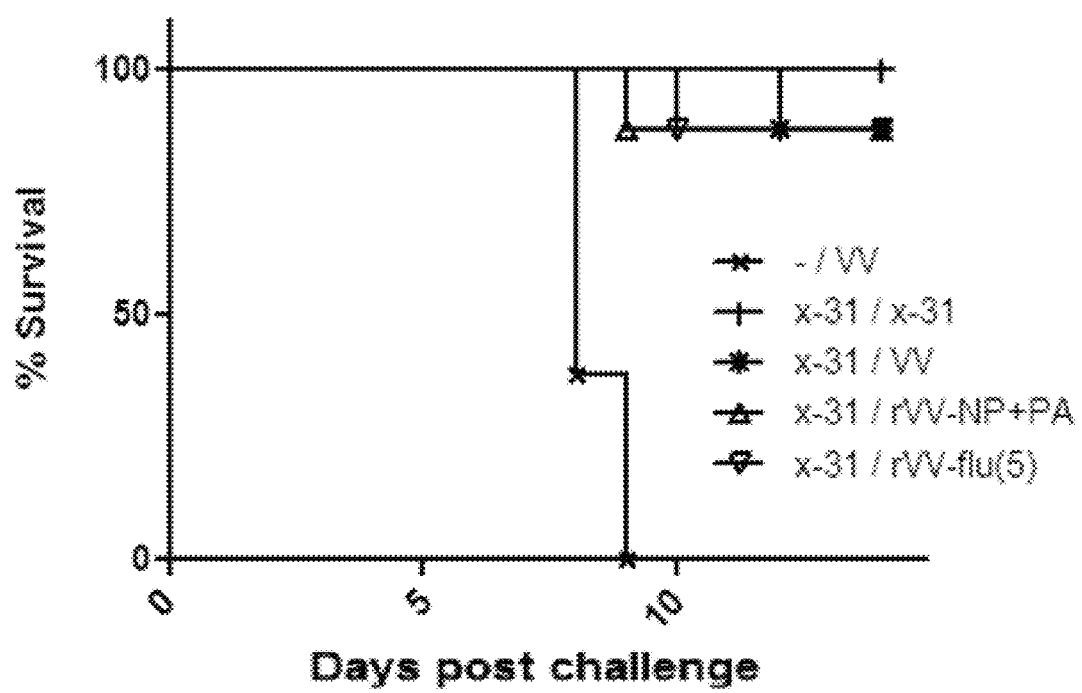

FIG. 8B shows graph depicting the weight loss and survival rate of x-31-prime-immunized C57BL/6 mice, which were challenged with HPAI H5N1 after 3 weeks of rVV-flu immunization (100 $LD_{50}$ A/MD/W401/11 (HPAI H5N1 field isolate)). The % survival were tracked for 2 weeks (each bar indicates average±standard error of measurement (SEM) for 8 mice/group).

Figure 8C:
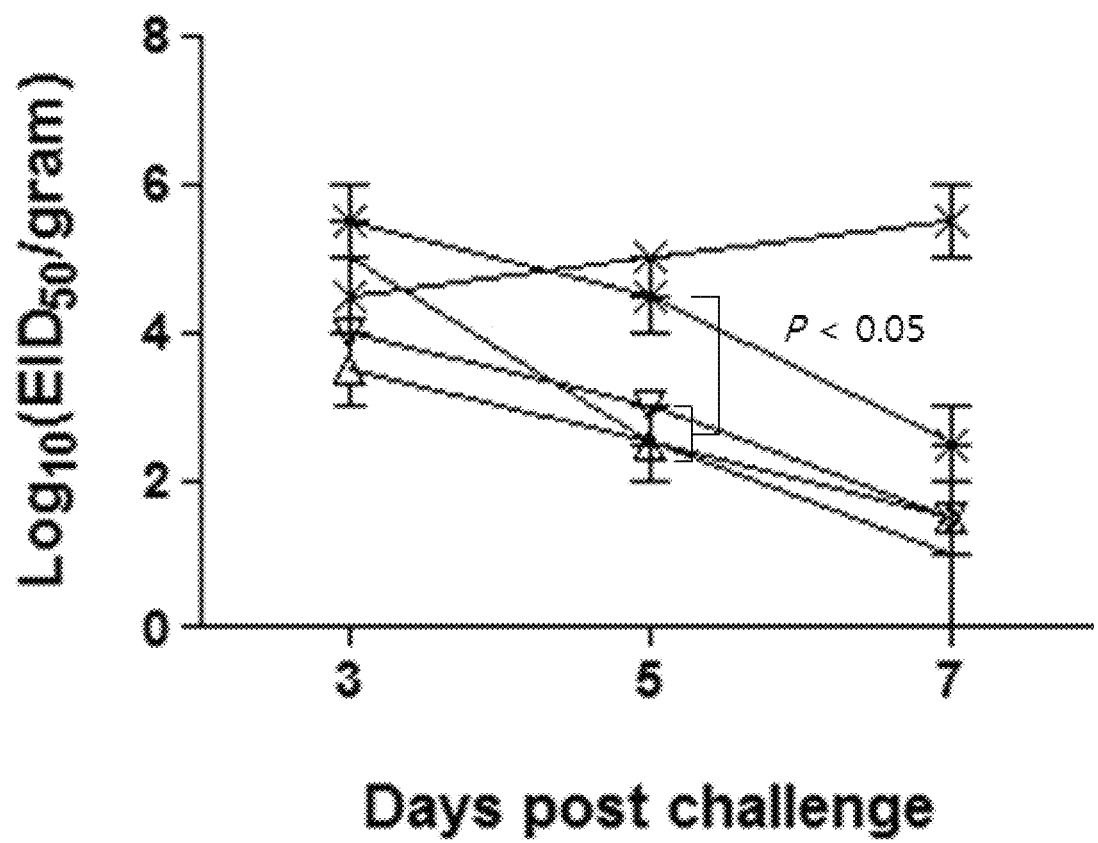

FIG. 8C shows a graph depicting the weight loss and survival rate of x-31-prime-immunized C57BL/6 mice, which were challenged with HPAI H5N1 after 3 weeks of rVV-flu immunization (100 $LD_{50}$ A/MD/W401/11 (HPAI H5N1 field isolate)). Lung virus titers were measured on day 3, 5, and 7 (each bar represents average±standard error of measurement (SEM) for 3 mice/group).

FIG. 9A shows a graph depicting cross-reactive IFN-γ-ELISPOT activity corresponding to CTL epitope, after the prime-immunized Phil/2/82 mice were subjected to rVV-flu immunization. The cross-reactive IFN-γ-ELISPOT activity was measured on CTL epitope of the priming virus (Phil/2/82) and the challenging virus (Cal/04/09). The above assay was conducted after 4 weeks of priming. (each bar indicates average±standard deviation (SD) for 2 mice/group).

Figure 9B:
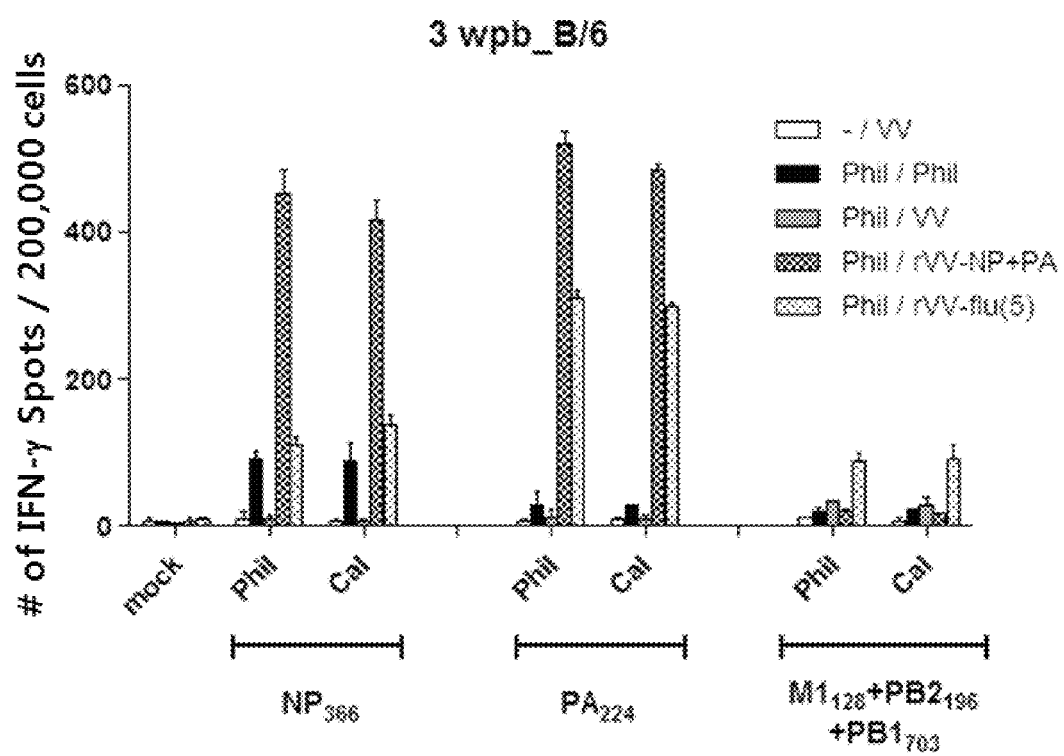

FIG. 9B shows a graph depicting cross-reactive IFN-γ-ELISPOT activity corresponding to CTL epitope, after the prime-immunized Phil/2/82 mice were subjected to rVV-flu immunization. The cross-reactive IFN-γ-ELISPOT activity was measured on CTL epitope of the priming virus (Phil/2/82) and the challenging virus (Cal/04/09). The above assay was conducted after 3 weeks of rVV-flu vaccination (each bar indicates average±standard deviation (SD) for 2 mice/group).

FIG. 10A shows a graph depicting the weight loss and survival rate of Phil/2/82-prime-immunized C57BL/6 mice, which were challenged with pandemic H1N1 adapted into mice after rVV-flu immunization. The mice were challenged with Cal/04/09 virus adapted into 100 $LD_{50}$ mice, after 3 weeks of immunization, and the % weight loss were observed (each bar indicates average±standard error of measurement (SEM) for 8 mice/group).

Figure 10B:
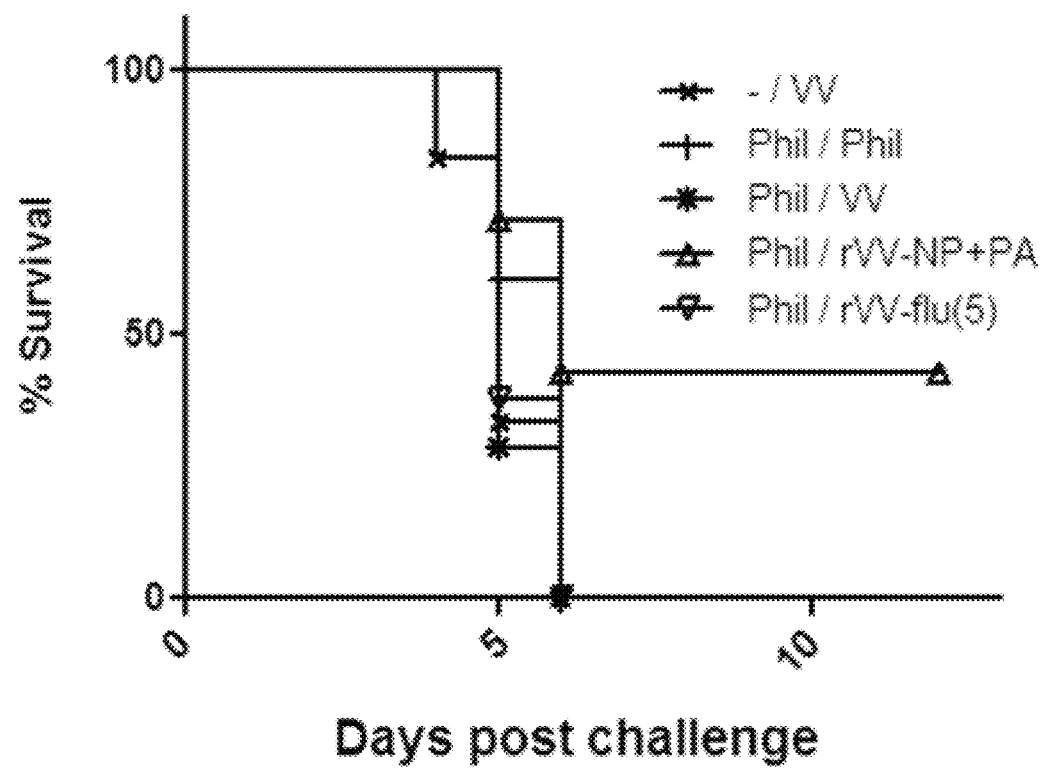

FIG. 10B shows a graph depicting the weight loss and survival rate of Phil/2/82-prime-immunized C57BL/6 mice, which were challenged with pandemic H1N1 adapted into mice after rVV-flu immunization. The mice were challenged with Cal/04/09 virus adapted into 100 $LD_{50}$ mice, after 3 weeks of immunization, and the % survival thereof were observed (each bar indicates average±standard error of measurement (SEM) for 8 mice/group).

DETAILED DESCRIPTION OF EMBODIMENTS

Hereinafter, the present invention will be described in detail with reference to examples and drawings. The examples are only for specifically explaining the present invention and it is obvious to those skilled in the art that the scope of the present invention is not limited by the examples according the gist of the present invention.

Preparation of Animal Model and Virus

C57BL/6 and Balb/c female mice of 6 weeks of age purchased from the Charles-River Laboratory (Orient Bio Inc., Sungnam, Korea) were used in the present invention. Parental NYCBH vaccinia variants were used for production of rVV-flu, and A/PR/8/34 (H1N1) and x-31 (H3N2) influenza viruses were used in the present invention. All procedures for using the H5N1 virus were conducted in a Biosafety Level-3 (BSL-3) facility.

Selection of Internal Genes Containing Consensus Sequence and Representative Sequence In order to determine the equidistant consensus sequence from bird, pig, and human influenza isolates, a total of 14,011 sequences of the influenza internal genes (PB2, PB1, PA, NP, M1, M2, NS1 and NS2) were searched from influenza virus data of the U.S. National Center for Biotechnology Information (NCBI) (http://www.ncbi.nlm.nih.gov/genomes/FLU/FLU.html).

In respective species, the individual gene phylogenetic tree was created by using a neighbor-joining method, and, finally, the consensus sequence of eight kinds of internal genes was determined. Three among the eight kinds of internal genes, NS1, NS2, and M2, were excluded in selection of the internal genes for the T-cell based universal flu vaccine of the present invention due to the following reasons:

(1) Since three kinds of internal genes are shorter than the other internal genes, the opportunities for presenting a defense T-cell epitope are limited;

(2) Since NS1 has been known to suppress Type I interferon response, it may influence the immunogenicity formation when a delivery vector using NS1 as an antigen is used; and (3) M2 does not contribute to the defense against a fatal dose of vaccination since the efficacy caused by the combination of rVV-NP+PA and rVV-flu (5) is significantly lower than the efficacy induced by single r-VV-M2 vaccination in an anti-M2 antibody response.

Therefore, five kinds of internal genes, NP, PA, PB1, PB2, and M1 were selected for the T-cell based universal flu vaccine of the present invention, and immunogenicity and efficacy thereof were analyzed.

GenBank Accession Numbers of the five kinds of internal genes and proteins translated therefrom are as follows:

NP gene (SEQ ID NO: 1), gi:323984, gb:M22574.1,

NP protein (SEQ ID NO: 2), gi:323985, gb:AAA43095.1;

PA gene (SEQ ID NO: 3), gi:78097605, gb:CY005610.1,

PA protein (SEQ ID NO: 4), gi:78097606, gb:ABB20301.1;

PB1 gene (SEQ ID NO: 5), gi:82654856, gb:CY005794.1,

PB1 protein (SEQ ID NO: 6), gi:82654857, gb:ABB88367.1;

PB2 gene (SEQ ID NO: 7), gi:134044357, gb:CY011035.2,

PB2 protein (SEQ ID NO: 8), gi:113901268, gb:ABI47980.1; and

M1 gene (SEQ ID NO: 9), gi:4584881, gb:AAD25173.1,

M1 protein (SEQ ID NO: 10), gi:4584882, gb:AAD25173.1,

TABLE 1

Numbers of influenza isolates and subgroups for determining final consensus sequences of influenza A internal genes.

|     | Number of influenza isolates analyzed | | | | Number of subgroups (selection criteria) (% Ave.a.a.identy ± SD) | | | | Final consensus sequence Average |
|-----|-------|------|------|-------|-------------|-------------|-------------|-------|---------|
|     | Human | Pig  | Bird | Total | Human       | Pig         | Bird        | Total | Distance |
| PB2 | 866   | 187  | 1303 | 2356  | 32 (>97%)   | 13 −96%     | 36 −97%     | 81    | 97.70%  |
| PB1 | 835   | 199  | 1213 | 2247  | 30 (>97%)   | 7 (>91%)    | 45 (>98%)   | 82    | 98.70%  |
| PA  | 826   | 190  | 1403 | 2419  | 18 (>97%)   | 12 (>94%)   | 31 (>96%)   | 61    | 9790%   |
| NP  | 581   | 187  | 920  | 1688  | 29 (>97%)   | 27 (>96%)   | 55 (>96%)   | 111   | 96.80%  |
| M1  | 255   | 130  | 525  | 910   | 19 (>97%)   | 18 (>97%)   | 28 −96%     | 65    | 97.70%  |
| M2  | 372   | 137  | 536  | 1045  | 32 (>91%) (95.0% ± 2.4%) | 32 (>93%) (95.5% ± 1.5%) | 29 (>91%) 94.7% ± 1.8%) | 93 | 92.50% |
| NS1 | 710   | 228  | 1419 | 2357  | 30 (>94%)   | 32 (>89%) (95.8% ± 2.6%) | 76 (>90%) (96.5% ± 2.2%) | 138 | 90.80% |
| NS2 | 256   | 111  | 622  | 989   | 20 (>97%)   | 15(>91%)    | 19(>91%)    | 54    | 94.40%  |
|     | Total |      |      | 14,011 |            |             |             | 685   | 97.10%  |

The T-cell based universal flu vaccine containing the five kinds of internal genes has higher immunogenicity than the control group. When comparing the conventionally known conserved human T-cell epitope with the consensus sequence from the influenza isolates, 1,142 amino acids among 1,147 amino acids of the conserved human T-cell epitope are 99.6% identical to the consensus sequence.

TABLE 2

Homology between known common epitope and consensus sequence of T-cell based universal flu vaccine of the present invention

|     | Total number of amino acids of epitope | Number of amino acids of homologous epitope | Homology % |
|-----|-----|-----|-------|
| PB2 | 366 | 365 | 99.7% |
| PB1 | 359 | 358 | 99.7% |
| PA  | 171 | 170 | 99.4% |

TABLE 2-continued

Homology between known common epitope and consensus sequence of T-cell based universal flu vaccine of the present invention

|     | Total number of amino acids of epitope | Number of amino acids of homologous epitope | Homology % |
|-----|-----|-----|-------|
| NP  | 149 | 148 | 99.3% |
| M1  | 102 | 101 | 99.0% |
| Total | 1147. | 1142 | 99.6% |

The internal genes of the present invention have average 95% sequence homology to the new influenza (2009 H1N1) (95.3% to A/Mexico/InDRE4114/2009; 95.2% to A/Canada-AB/RV1532/2009; and 95.0% to A/New York/1669/2009), and average 97.8% amino acid homology to the influenza isolates from influenza virus data of the U.S. National Center for Biotechnology Information (NCBI). The above homology level means that the present invention can achieve broad T-cell-mediated defense against some unknown epidemic influenza.

TABLE 3

Homology between influenza isolates from influenza virus data of the U.S. National Center for Biotechnology Information (NCBI) and consensus sequence of T-cell based universal flu vaccine of the present invention

|     | Number of amino acids | 100% identical | % Homology of influenza variant having consensus sequence (% range of influenza isolates in influenza database)* | | | | |
|-----|------|-----------------|---------|---------|---------|---------|---------|
|     |      |                 | Average distance | PR/8/34 (H1N1) | Mallard/ W401/11 (H5N1) | Philippinne/ 2/82 (H3N2) | California/ 04/09 (H1N1) |
| PB2 | 759  | A/blue-winged Teal/Ohio/926/ 2002 (H3N8) | 97.7% | 97.2% (63.5%) | 98.4% (57.8%) | 95.5% (75.6%) | 97.8% (59.3%) |
| PB1 | 758  | A/turkey/Italy/4169/ 1999 (H7N1) | 98.7% | 97.6% (87.5%) | 98.5% (63.9%) | 98.8% (63.3%) | 97.1% (87.9%) |
| PA  | 716  | A/chicken/ Hong Kong/ 17/1977 (H6N1) | 97.9% | 97.2% (65.2%) | 99.2% (38.1%) | 95.4% (81.2%) | 97.5% (63.5%) |
| NP  | 498  | A/duck/Bavaria/2/ 1977 (H1N1) | 96.8% | 94.6% (69.3%) | 98.0% (55.0%) | 92.4% (86.4%) | 94.6% (69.3%) |

TABLE 3-continued

Homology between influenza isolates from influenza virus data of the U.S. National Center for Biotechnology Information (NCBI) and consensus sequence of T-cell based universal flu vaccine of the present invention

| | Number of amino acids | 100% identical | % Homology of influenza variant having consensus sequence (% range of influenza isolates in influenza database)* | | | | |
|---|---|---|---|---|---|---|---|
| | | | Average distance | PR/8/34 (H1N1) | Mallard/ W401/11 (H5N1) | Philippinne/ 2/82 (H3N2) | California/ 04/09 (H1N1) |
| M1 | 257 | A/chicken/ New York/ 13142-5/94 (H7N2N5B) | 97.7% | 96.8% (67.3%) | 96.4% (86.0%) | 97.2% (57.6%) | 96.5% (67.3%) |
| Total number of Amino acids | 2983 | 100.0% | 97.8% | 96.7% (71.3%) | 98.1% (56.5%) | 95.9% (74.1%) | 95.9% (69.9%) |

*Range (%) of influenza isolates in influenza virus data of the U.S. National Center for Biotechnology Information (NCBI), which share higher homology than variant appeared in the consensus sequence: PB2 (n = 2356), PB1 (n = 2247), PA (n = 2419), NP (n = 1688), M1 (n = 910).

EXAMPLE 1

Production of rVV-flu Vaccine

In order to produce r-VV flu vaccine, influenza gene-optimized human codons were synthesized, and inserted at the EcoRV site of pUc57 (provided by GenScript (Piscataway, N.J.). Each plasmid containing NP or MI gene was cut by AscI/SbfI restriction enzymes, and then the cut pBMSF7C vaccine delivery vector was linked thereto by PstI/AscI. An appropriate size of PB2, PB1, and PA were inserted into the cut fragments of pUC57 by AscI/SbfI, and then the vector was cut by DraI restriction enzyme one more time. The cut pBMSF7C was cloned by PstI/AscI. The rVV-flu vaccine was produced by slightly changing the conventional method thereof (Vaccine 25,630-637, 2007). BHK-21 cells infected with vaccinia virus at multiplicitiy of infection (MOI) of 10 were transfected with pBMSF7C-flu. The viruses were harvested after 24 hours of transfection, and RK-13 cells, from which recombinant HA negative plaques are to be screened, were again infected therewith. After 3 days of infection, the cells were reacted with turkey RBC at 37° C. for 30 minutes to isolate HA negative plaques. The HA negative plaques were continuously cloned until HA positive plaques disappeared, and then confirmed by HA staining of ~1,000 plaques per 100-mm dish. The final recombinant viruses were purified, and amplified in BHK-21 cells (0.1 MOI). They were low-temperature stored at −80° C. prior to the use thereof.

It was confirmed whether the influenza genes are inserted into the recombinant vaccinia virus by using the PCR method, and the final clones were confirmed by Western blot and sequencing of binding sites.

EXAMPLE 1-1

Western Blot Assay of rVV-flu

BHK-21 cells were infected with rVV-flu at MOI of 0.1 for 1 hour. Then, the cells were incubated for three days, followed by harvesting. Proteins were extracted with an M-PER buffer solution according to the conventionally known existing method (Pierce, Rockford, Ill.). Thermo-denatured proteins were separated by 4-12% SDS-PAGE (Invitrogen Carlsbad, Calif.), and transferred on the nitrocellulose membrane (Invitrogen Carlsbad, Calif.). The membrane was blocked in a PBS buffer solution containing 0.2% Tween 20 together with 5% nonfat milk for 1 hour, and reacted with primary antibodies.

The following antibodies were used for detection:
anti-PB2 (Santacruz Carlsbad, Calif.);
anti-PB1 (Santacruz Carlsbad, Calif.);
anti-PA (Peptron Inc., Daejeon, Korea);
anti-NP and anti-M1 (X-31/PR8 immunized mouse serum).

The membrane was incubated together with horseradish peroxidase-labeled anti-mouse IgG antibodies (KPL Gaithersburg, Md.), and stained with ECL plus kit (Amersham Buckinghamshire, U.K.).

EXAMPLE 2

Immunogenicity Evaluation of rVV-flu

EXAMPLE 2-1

IFN-γ ELISPOT Assay

Figure 1:
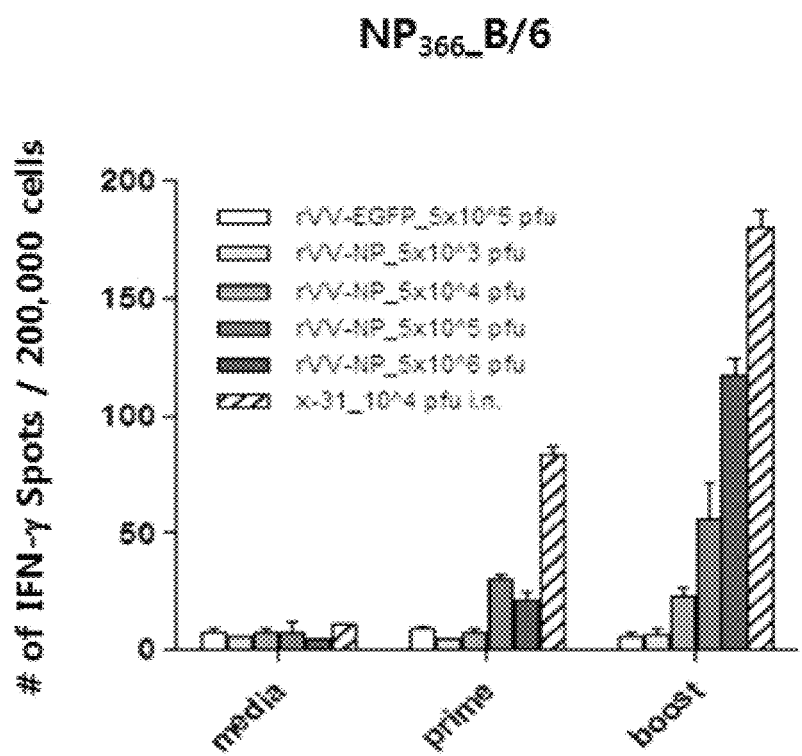
FIG. 1 shows graph depicting T-cell immunogenicity according to the concentration of rVV-NP vaccine administered to C57BL/6 mice by skin scarification. rVV-EGFP as a negative control was administered by skin scarification, and x-31 as a positive control was intranasally administered. The splenocytes stimulated with $NP_{366}$ CTL epitope peptides after 4 weeks of immunization were analyzed by IFN-γ-ELISPOT assay (each bar indicates average±standard deviation (SD) for 2 mice/group.

In the present invention, immunogenicity of rVV-flu was evaluated through IFN-γ ELISPOT assay in order to determine the optimum vaccine combination in vaccinia based influenza vaccination. High immunogenicity of nucleoprotein (NP) was confirmed in the H-2b mouse model. Several doses of rVV-NP were administered through the conventionally known skin scarification (s.s.), and immunogenicity due to this was induced according to the administration dose In T-cell response. It was confirmed that the boosting immunization improved the T-cell response (see, FIG. 1).

Figure 2:
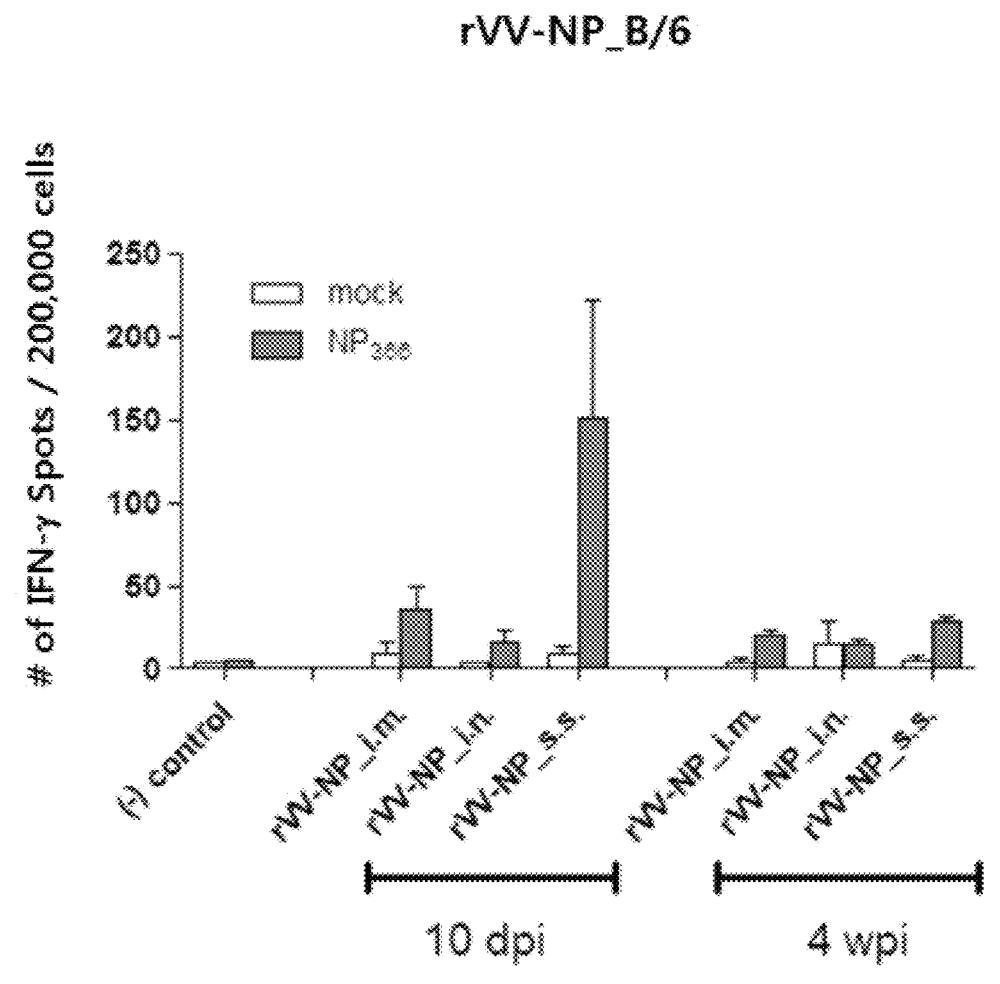

In the present invention, the administration of vaccine was performed by an intramuscular (i.m.) method, an intranasal (i.n.) method, or a skin scarification (s.s.) method. Here, the skin scarification (s.s.) method was most preferable since it exhibits 5 times higher immunogenicity than the intramuscular (i.m.) method or the intranasal (i.n.) method (see, FIG. 2).

Since 91~98% of humans have been infected with influenza virus, they have influenza-specific memory T-cells. Therefore, in the present invention, influenza-prime-immunized mice were used as a mouse model for evaluating immunogenicity and efficacy of vaccine. Among four combinations of the intramuscular (i.m.) method and the intranasal (i.n.) method, x-31 intramuscular priming/intranasal boosting administration method induced the highest level of T-cell immunity (see, FIG. 3).

The x-31-prime-immunized C57BL/6 mice were challenged with $10^6$ pfu of vaccinia influenza, and the Balb/c mice were challenged with $10^6$ pfu of vaccinia influenza.

In the C57BL/6 mice, immunogenically predominant epitopes of the following two kinds of T-cell based universal flu vaccine were $NP_{366}$ and $PA_{224}$, and 90% or more of flu-specific T-cell response could be induced (see, FIGS. 4A to 4F).

rVV-NP+PA
rVV-flu (5) (Flu (5) means internal genes, NP, PA, PB1, PB2, and M1.)

The epitopes of NP and PA, $NP_{366}$ and $PA_{224}$, exhibited the most predominant immunogenicity in flu-specific T-cell response. However, vaccine containing T-cell epitopes obtained from the five kinds of internal genes is provided, to thereby allow human to prepare for a case where NP and PA are contained as T-cell epitope.

EXAMPLE 3

Immunization Using Mouse Model 5 ul of $10^4$ pfu of X-31 was administered to the mice through the intranasal (i.n.) route without anesthesia (priming immunization, on day 0). The mice were vaccinated with 5 ul of $10^6$ pfu of rVV-flu by skin scarification (s.s.) administration (boosting immunization, on day 28).

The parental-VV was used alone as a negative control. The priming vaccination of a positive control of 50 ul was performed on the thigh muscle at the rear parts of both hind legs through the intramuscular (i.m.) route, and the boosting vaccination was performed by using the intranasal (i.n.) route ($10^4$ pfu of x-31).

Eight mice were used for each group. On the day after three weeks of the immunization, the mice were anesthetized with avertin, and infected with 50 ul of A/PR/8/34 virus at $LD_{50}$ of 0.5/10/100.

As the hetero-subtypic flu virus, 100 $LD_{50}$ highly pathogenic H5N1 A/Mallard Duck/Korea/W401/11 and epidemic A/California/04/09 were used. The survival and the change in weight of the mice were confirmed everyday for 2 weeks, and the mice were euthanized when they lost 30% or more of the initial weight for animal welfare (see, FIGS. 6, 7A to 7F, 10A and 10B).

EXAMPLE 4

Preparation of Lung Cells for Cell Immunity

The lung cells were disrupted following the conventionally known protocol (Miltenyi Biotec Inc., Carlsbad, Calif.). The disrupted lung cells were treated with RBC lysis buffer on ice for 5 minutes (Sigma-Aldrich). The lung cells with the removal of RBC were disentangled in RPMI, and in vivo apoptosis effect (in vivo CTL) assay and ELISPOT (Enzyme-Linked ImmunoSpot) assay were conducted.

EXAMPLE 5

Ex-Vivo IFN-γ ELISPOT Assay

The ELISPOT assay was conducted using the mouse IFN-γ ELISPOT$^{PLUS}$ kit (Mabtech, AB Nacta Strand, Sweden).

$2 \times 10^5$ fresh splenocytes or lung cells were plated on the 96-well plate coated with anti-mouse IFN-γ capture antibody, and stimulated with 1 μM of influenza peptide epitope (Peptron, Daejeon, Korea) or EL4 ($2 \times 10^5$ cells/well) infected with 1 MOI of PR8 virus for 18 hours.

The flu-specific CD8+ T-cell epitope was as follows:

| | |
|---|---|
| $NP_{366-74}$ | (Db, ASNENMETM); |
| $PA_{224-33}$ | (Db, SSLENFRAYV); |
| $PB2_{196-210}$, | (Db or Kb, CKIAPLMVAYMLERE); |
| $PB1_{703-11}$ and | (Kb, SSYRRPVGI); |
| $M1_{128-35}$ | (Kb, MGLIYNRM). |

The splenocytes pulsed with $PB2_{198-206}$ or infected with B/Malaysia/2506/04 were used in a level of 8±5(SD) and 13±9(SD) per well for a negative control. The lung cells were used in a higher level for a higher negative control (14±13 and 25±26). The number of IFN-γ secretion cells ((ISCs) was measured using an ELISPOT reader (AID, Strassberg, Germany) (See, FIGS. 5A to 5C).

EXAMPLE 6

In Vivo Cytotoxic T-Cell (CTL) Assay

The splenocytes obtained from naive mice were stained with 5 M PKH26 (Sigma-Aldrich, Saint Louis, Mo.) at room temperature for 10 minutes. Labeling was stopped by addition of the same amount of FBS, followed by incubation for 1 minute. Additional staining with 0.5 uM, 2 uM, or 8 uM of CFSE (Carboxy Fluorescein Succinimidyl Ester) was conducted at 37° C. for 10 minutes, and then stopped by addition of the same amount of FBS, followed by incubation for 1 minute. The doubly stained cells were stimulated with the indicator epitope peptide (1 uM) at 37° C. for 1 hour.

Each target cell and a different peptide were mixed together, and the mixture was administered to the naive or immunized mice through intravenous (i.v.) administration. After 12 hours of administration, single cell dispersions of the splenocytes and lung cells were prepared, and activity of in vivo cytotoxic T cell (CTL) was measured using flow cytometry analysis (BD LSRFortessa, Bioscience BD, Piscataway, N.J.). The cell killing ratio (%) was calculated according to the following equation.

$$\text{Cell killing ratio (\%)} = 100 - \left\{ \frac{\text{(number of stimulated target cells remaining in the immunized mouse/number of un-stimulated target cells remaining in the immunized mouse)}}{\text{(number of stimulated target cells remaining in the naïve mouse/number of un-stimulated target cells remaining in the naïve mouse)}} \times 100 \right\}$$ [Equation]

EXAMPLE 7

In Vivo Cytokine Staining (ICS) and T Cell Polyfunctionality Analysis

In the present example, polyfunctionality of influenza specific T cell induced by rVV-flu vaccine was observed. After rVV-flue immunization, stimulations with $NP_{366}$(upper panel) and $PA_{224}$ (lower panel) epitopes were conducted for 7 days. Secretion of IFN-γ, TNF-α and IL-2 cytokines and expression of degranulation markers (CD107a) were measured by in vivo cytokine staining (see, FIGS. 5A to 5C).

In the presence of anti-CD107a-PE-Cy7 (BD Biosciences), the splenocytes were stimulated with cytotoxic T cell (CTL) epitope peptide (1 ug/ml) such as $NP_{366}$ or $PA_{224}$, and, after 1 hour, monesin (GolgiStop, BD Biosciences), which is a kind of transferring antibiotic materials for improving cell permeability, was added. After 5 hours of incubation, the splenocytes were stained with ethidium monoazide, and anti-CD3-Horizon V500, anti-CD4-Horizon V450, and anti-CD8-APC-H7 (BD Biosciences) were stained with ethidium monoazide. They were permeabilized using Cytofix/Cytoperm kit (BD Biosciences) and further stained with anti-IL-2-FITC (eBioscience), anti-IFN-γ-APC (BD Biosciences) and anti-TNF-PE (BD Biosciences). FACS assay was conducted using an LSRII flow cytometer (BD Biosciences), and data were analyzed by FlowJo software (Treestar, San Fran Carlos, Calif.). Quantification and analysis of T cells with respect to various combinations of cytokines and degranulation were conducted by using FlowJo software.

Influenza HA is a main target for monitoring antibody-mediated host immunity, and variation thereof continuously occurs. Therefore, only influenza HA having a consensus sequence has an advantage of cross-defense. The internal genes have relatively low immunity than HA, and thus have been significantly conserved. The conserved sequence of the present invention is characterized by having sufficient cell immunity for allowing the cross-reaction since it has average 97.8% homology The present invention is characterized by selecting the entire internal genes in their original states, instead of epitope sequences of providing customized antigen representation of T cell epitope according to individual HLA polymorphism. In addition, the multi-epitope-specific T cell response can decrease the possibility of variant formation. Notwithstanding the use of the multi-gene, the decrease in immunogenicity of individual antigen is due to antigen competition among individual recombinant viruses in replication of T cells and antigen presentation. This was demonstrated from antigen competition in the DNA vaccine combination study. In the present invention, cross-reactive IFN-γ-ELISPOT activity was measured with respect to CTL epitopes of the priming virus (Phil/2/82) and the challenging virus (Cal/04/09). The assay was conducted after 4 weeks of priming (a) and after 3 weeks of rVV-flu vaccination (see, FIGS. 9A and 9B).

EXAMPLE 8

Titer Assay of Lung Virus

The mice infected with influenza were enthanized after 3, 5, and 7 days, to obtain lung tissues thereof. The obtained lung tissues were disrupted in 10% W/V serum free Minimum Essential Me-dia (MEM) for analyzing virus titer using plaque assay. The limit of virus detection was 100 pfu/g of the lung (this value corresponds ~20 pfu/mouse). The titer of HPAI H5N1 virus was measured by using the eggs in BSL3+ facilities received approval for influenza experiment. The limit of virus detection was 0.7 log 10 $EID_{50}$/ml or lower (see, FIGS. 7A to 7F, and 8A to 8C).

The differences in weight loss and lung virus titer between groups were analyzed by the Student T test. The difference in survival was calculated by the Fisher's exact test, and it was confirmed that the statically significant p value was 0.05 or lower (see, FIGS. 7A to 7F, and 8A to 8C).

The T cell-based universal influenza vaccine of the present invention includes at least one CTL epitope in each of the internal genes, and thus can enhance immunogenicity thereof according to combination of the internal genes, and thereby can defend against various hetero-subtypic variants of the influenza viruses.

What is claimed is:

1. A T cell-based immunogenic composition comprising an influenza M1 gene having the sequence of SEQ ID NO:9, further comprising at least one additive selected from the group consisting of pharmaceutically acceptable immunopotentiator, carrier, excipient, and diluent.

2. The T cell-based immunogenic composition of claim 1, further comprising at least one influenza gene selected from the group consisting of an NP gene having the sequence of SEQ ID NO:1, a PA gene having the sequence of SEQ ID NO:3, a PB1 gene having the sequence described by SEQ ID NO: 5, and a PB2 gene having the sequence described by SEQ ID NO: 7.

3. A T cell-based immunogenic composition comprising all of NP (SEQ ID NO: 1), PA (SEQ ID NO: 3), PB1 (SEQ ID NO: 5), PB2 (SEQ ID NO: 7), and M1 (SEQ ID NO: 9) gene.

4. The T cell-based immunogenic composition of claim 2, wherein the NP (SEQ ID NO: 1), PA (SEQ ID NO: 3), PB1 (SEQ ID NO: 5), PB2 (SEQ ID NO: 7), and M1 (SEQ ID NO: 9) gene each encodes at least one CTL epitope.

5. The T cell-based immunogenic composition of claim 2, wherein the CTL epitope of the NP protein is MASQGTKRSYEQMET (SEQ ID NO: 11), GIGRFYIQMCTELKL (SEQ ID NO: 12), MVLSAFDERRN (SEQ ID NO: 13), YLEEHPSAGKDPKKTGGPIY (SEQ ID NO: 14), LYDKEEIRRIWRQANNG (SEQ ID NO: 15), ATYQRTRAL (SEQ ID NO: 16), YERMCNILKG (SEQ ID NO: 17), QVRESRNPGNAEIEDLIFLA (SEQ ID NO: 18), QLVWMACHSAAFEDLRVSSF (SEQ ID NO: 19), or QPTFSVQRNLPF (SEQ ID NO: 20);

the CTL epitope of the PA protein is KIETNKFAAICTHLEVCFMYSDFHF (SEQ ID NO: 21), RTMAWTVNSI (SEQ ID NO: 22), VEKPKFLPDLY (SEQ ID NO: 23), YYLEKANKIKSE (SEQ ID NO: 24), THIHIFSFTGEEMA (SEQ ID NO: 25), RGLWDSFRQSERGEETIEE (SEQ ID NO: 26), RSKFLLMDALKLSIE (SEQ ID NO: 27), HEGEGIPLYDAIKC (SEQ ID NO: 28), SQLKWALGENMA (SEQ ID NO: 29), EFNKACELTDSSWI (SEQ ID NO: 30), SRPMFLYVRTNGTSK (SEQ ID NO: 31), or AESRKLLLI (SEQ ID NO: 32);

the CTL epitope of the PB1 protein is DVNPTLLFLKVPAQNAISTTFPYTGDPPYSHGTGTGYTMDTVNRTHQYSE (SEQ ID NO:33), MAFLEESHPGIFENS (SEQ ID NO: 34), VQQTRVDKLTQGRQTYDWTLNRNQPAATALANTIE (SEQ ID NO: 35), TKKMVTQRTIGKKK (SEQ ID NO: 36), FVETLARSICEKLEQSGL (SEQ ID NO: 37), RMFLAMITYITRNQP (SEQ ID NO: 38), LSIAPIMFSNKMARLGKGYMFESKSMKLRTQIPAEMLA (SEQ ID NO: 39), SPGMMMGMFNMLSTVLGVS (SEQ ID NO: 40), GINMSKKKSYIN (SEQ ID NO: 41), TGTFEFTSFFYRYGFVANFSMELPSFGVSGINESADMSI (SEQ ID NO: 42), GVTVIKNNMINNDLGPATAQMALQLFIKDYRYTYRCHRGDTQIQTRRSFE (SEQ ID NO: 43), VSDGGPNLY (SEQ ID NO: 44), MEYDAVATTHSW (SEQ ID NO: 45), PKRNRSILNTSQRGILEDEQMYQ (SEQ ID NO: 46), or AEIMKICST (SEQ ID NO: 47);

the CTL epitope of the PB2 gene is LMSQSRTREILTKTTVDHMAIIKKYTSGRQEKNP (SEQ ID NO: 48), WMMAMKYPI (SEQ ID NO: 49), PERNEQGQTLWSK (SEQ ID NO: 50), PLAVTWWNRNGP (SEQ ID NO:51), GPVHFRNQVKIRR (SEQ ID NO: 52), YIEVLHLTQGTCW (SEQ ID NO: 53), EQMYTPGGEV (SEQ ID NO: 54), NDDVDQSLIIAARNIVRRA (SEQ ID NO: 55), ASLLEMCHSTQIGG (SEQ ID NO: 56), SFSFGGFTFK (SEQ ID NO: 57), LTGNLQTLK (SEQ ID NO: 58), RVHEGYEEFTMVG (SEQ ID NO: 59), RATAILRKATRR (SEQ ID NO: 60), VAMVFSQEDCM (SEQ ID NO: 61), KAVRGDLNF (SEQ ID NO: 62), VNRANQRLNPMHQLLRHFQKDAKVLF (SEQ ID NO: 63), RVSKMGVDEYS (SEQ ID NO: 64), GNVLLSPEEVSETQG (SEQ ID NO: 65), LTITYSSSMMWEINGPESVL (SEQ ID NO: 66), NTYQWIIRNWE (SEQ ID NO: 67), MLYNKMEFEPFQSLVPKA (SEQ ID NO: 68), LGTFDTVQIIKLLPFAAAPP (SEQ ID NO: 69), QSRMQFSSLTVNVRGSGMRILVRGNSPVFNYN (SEQ ID NO: 70), or GVESAVLRGFLI (SEQ ID NO: 71); and the CTL epitope of the M1 protein is SLLTEVETYVL (SEQ ID NO: 72), KTRPILSPLTKGIL (SEQ ID NO: 73), GFVFTLTVPSE (SEQ ID NO: 74), LYRKLKREITF (SEQ ID NO: 75), ALASCMGLIY (SEQ ID NO: 76), MGTVTTEVAFGLVCA (SEQ ID NO: 77), NRMVLASTTAKAMEQMAGSS (SEQ ID NO: 78), or QARQMVQAMR (SEQ ID NO: 79).

6. The T cell-based immunogenic composition of claim 2, wherein the genes are included in a recombinant virus.

7. The T cell-based immunogenic composition of claim 6, wherein the recombinant virus is a recombinant vaccinia virus, a recombinant adenovirus, a recombinant adeno associated virus, a recombinant retrovirus, or a recombinant lentivirus.

8. The T cell-based immunogenic composition of claim 7, wherein the recombinant virus is the recombinant vaccinia virus.

9. The T cell-based immunogenic composition of claim 7, wherein it is administered through a skin scarification (s.s) route, an intramuscular (i.m.) route, an intranasal (i.n.) route, an intradermal (i.d.) route, an intravenous (i.v.) route, or an intraperitoneal (i.p.) route.

10. The T cell-based immunogenic composition of claim 9, wherein it is administered through the skin scarification (s.s.) route.

* * * * *